US007026283B2

(12) United States Patent
Fleming et al.

(10) Patent No.: US 7,026,283 B2
(45) Date of Patent: Apr. 11, 2006

(54) CALCIUM-INDEPENDENT NEGATIVE REGULATION BY CD81 OF RECEPTOR SIGNALLING

(75) Inventors: Tony Fleming, Stow, MA (US); Jean-Pierre Kinet, Lexington, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 371 days.

(21) Appl. No.: 10/004,562

(22) Filed: Dec. 5, 2001

(65) Prior Publication Data

US 2002/0182726 A1 Dec. 5, 2002

Related U.S. Application Data

(63) Continuation of application No. 08/954,279, filed on Oct. 20, 1997, now Pat. No. 6,423,501.

(60) Provisional application No. 60/032,963, filed on Dec. 13, 1996.

(51) Int. Cl.
*A61K 39/395* (2006.01)
*A61K 39/00* (2006.01)
*C12N 15/00* (2006.01)

(52) U.S. Cl. .................... 514/2; 424/139.1; 435/7.1; 530/300; 530/350; 530/387.9; 530/388.1

(58) Field of Classification Search ............ 514/2; 424/141.1, 130.1, 198.1; 435/7.1, 375; 436/547; 530/300, 350
See application file for complete search history.

(56) References Cited

OTHER PUBLICATIONS

Tanaka, M., et al., "IgE-Mediated Hypersensitivity and Contact Sensitivity to Multiple Environmental Allergens in Atopic Dermatitis," *Arch. Dermatol.*, 130(11):1393-1401 (1994) (Abstract only).
Sussman, G. L., and Beezhold D. H., "Allergy to Latex Rubber," *Ann. Intern. Med.*, 122(1):43-46 (1995).
Kuby, J., "Hypersensitive Reaction," In *Immunology, Second Edition*, (NY: W. H. Freeman and Company), pp. 129 and 417-443 (1994).
Maecker, H. T., et al., "CD81 on B Cells Promotes Interleukin 4 Secretion and Antibody Production During T Helper Type 2 Immune Responses," *Proc. Natl. Acad. Sci. USA*, 95:2458-2462 (1998).
Maurer, D., et al., "Peripheral Blood Dendritic Cells Express FcεRI as a Complex Composed of FcεRIα-and FcεRIγ-Chains and an Use This Receptor for IgE-Mediated Allergen Presentation," *J. Immun.*, 607-616 (1996).
Pileri, P., et al., "Binding of Hepatitis C. Virus to CD81," *Science* (282):938-941 (1998).

Jouvin, M-H.E., et al., "Differential Control of the Tyrosine Kinases Lyn and Syk by the Two Signaling Chains of the High Affinity Immunoglobulin E Receptor", *The Journal of Biological Chemistry*, 269(8):5918-5925 (1994).
Penhallow, R.C., et al., "Temporal Activation of Nontransmembrane Protein-Tyrosine Kinases Following Mast Cell FcεRI Engagement", *The Journal of Biological Chemistry*; 270(40) :23362-23365 (1995).
Scharenberg, A.M., et al., "Reconstitution of Interactions Between Tyrosine Kinases and the High Affinity IgE Receptor Which Are Controlled by Receptor Clustering", *The EMBO Journal*, 14(14) :3385-3394 (1995).
Lin, S., et al., "The FcεRIβ Subunit Functions as an Amplifier of FcεRIγ-Mediated Cell Activation Signals", *Cell*, 85:985-995 (1996).
Paul, W.E., et al., "Lymphokine and Cytokine Production by FcεRI+Cells", *Advances in Immunology*, 53:1-29 (1993).
Scharenberg, A.M. and Kinet, J-P., "Early Events in Mast Cell Signal Transduction", *Chem. Immunol.*, 61:72-87 (1995).
Ravtech, J.V. and Kinet, J-P., "Fc Receptors", *Annu. Rev. Immunol.*, 9:457-492 (1991).
Shaw, A.S., et al., "Interactions of TCR Tyrosine Based Activation Motifs with Tyrosine Kinases", *Immunology*, 7:13-20 (1995).
Choi, O.H., et al., "Calcium Mobilization via Sphingosine Kinase in Signalling by the FcεRI Antigen Receptor", *Nature*, 380:634-636 (1996).
Guthmann, M.D., et al., "A Secretion Inhibitory Signal Transduction Molecule on Mast Cells is Another C-Type Lectin", *Proc. Natl. Acad. Sci.*, 92:9397-9401 (1995).
Katz, H.R., et al., "Mouse Mast Cell gp49B1 Contains Two Immunoreceptor Tyrosine-Based Inhibition Motifs and Suppresses Mast Cell Activation When Coligated with the High-Affinity Fc Receptor for IgE", *Proc. Natl. Acad. Sci.*, 93:10809-10814 (1996).
Wright, M.D. and Tomlinson, M.G., "The Ins and Outs of the Transmembrane 4 Superfamily", *Immunology Today*, 15(12) :588-594 (1994).
Fearon, D.T and Carter, R.H., "The CD19/CR2/TAPA-1 Complex of B Lymphocytes: Linking Natural to Acquired Immunity", *Annu Rev. Immunol.* 13:127-149 (1995).
Secrist, H., et al., "Ligation of TAPA-1 (CD81) or Major Histocompatibility Complex Class II in Co-Cultures of Human B and T Lymphocytes Enhances Interleukin-4 Synthesis by Antigen-Specific Cd4'T Cells", *Eur. J. Immunol.*, 26:1435-1442 (1996).
Todd, S.C., et al., "CD81 Expressed on Human Thymocytes Mediates Integrin Activation and Interleukin 2-Dependent Proliferation", *J. Exp. Med.*, 184:2055-2060 (1996).

(Continued)

*Primary Examiner*—Joseph Murphy
*Assistant Examiner*—Nirmal S. Basi
(74) *Attorney, Agent, or Firm*—Hamilton, Brook, Smith & Reynolds, P.C.

(57) ABSTRACT

Calcium independent CD81 inhibition of IgE-mediated degranulation in mast cells, particularly through the FcγRIII and FcεRI receptors, is described, as well as methods of inhibiting allergic processes.

16 Claims, 13 Drawing Sheets

OTHER PUBLICATIONS

Oren, R., et al., "TAPA-1, the Target of an Antiproliferative Antibody, Defines a New Family of Transmembrane Proteins", *Molecular and Cellular Biology*, 10(8) :4007-4015 (1990).

Boismenu, R., et al., "A Role for CD81 in Early T Cell Development", *Science*, 271:198-200 (1996).

Imai, T., et al., "Molecular Analyses of the Association of CD4 with Two Members of the Transmembrane 4 Superfamily, CD81 and CD82", *The Journal of Immunology*, 155: 1229-1239 (1995).

Angelisovà, P., et al., "Association of Four Antigens of the Tetraspans Family (CD37, CD53, TAPA-1, and R2/C33) with MHC Class II Glycoproteins", *Immunogenetics*, 39: 249-256 (1994).

Mannion, B.A., et al., "Transmembrane-4 Superfamily Proteins CD81 (TAPA-1), CD82, CD63, and CD53 Specifically Associate with Integrin $\alpha_4\beta_1$ (CD49d/CD29)", *The Journal of Immunology*, 157 :2039-2047 (1996).

Berditchevski, F., et al., "A Novel Link Between Integrins, Transmembrane-4 Superfamily Proteins (CD63 and CD81), and Phosphatidylinositol 4-Kinase", *The Journal of Biological Chemistry*, 272(5) :2595-2598 (1997).

Ono, M., et al., "Role of the Inositol Phosphatase SHIP in Negative Regulation of The Immune System by the Receptor FcγRIIB", *Nature*, 383:263-266 (1996).

Burshtyn, D.N., et al., "Recruitment of Tyrosine Phosphatase HCP by the Killer Cell Inhibitory Receptor", *Immunity*, 4:77-85 (1996).

Galli, S.J., "New Concepts About the Mast Cell", *The New England Journal of Medicine*, 328(4) :257-265 (1993).

Maecker, H.T. and Levy, S., "Normal Llymphocyte Development but Delayed Humoral Immune Response in CD81-null Mice", *J. Exp. Med.*, 185(8) :1505-1510 (1997).

Miyazaki, T., et al., "Normal Development But Differentially Altered Proliferative Responses of Lymphocytes in Mice Lacking CD81", *EMBO J.*, 16(14) :4217-4225 (1997).

Tsitsikov, E.N., et al., "Impaired CD19 Expression and Signaling, Enhanced Antibody Response to Type II T Independent Antigen and Reduction of B-1 Cells in CD81-Deficient Mice", *Proc. Natl. Acad. Sci., USA*, 94:10844-10849 (1997).

Andria, M. L., et al., "Genomic Organization and Chromosomal Localization of the TAPA-1 Gene", *The Journal of Immunology*, 147(3) :1030-1036 (1991).

Levy, Shoshana, et al., "Structure and Membrane Topology of TAPA-1", *The Journal of Biological Chemistry*, 266(22):14597-14602 (1991).

Benhamou, M., et al., "Protein Tyrosine Kinases in Activation Signal of Human Basophils Through the Immunoglobulin E Receptor Type I", *Journal of Leukocyte Biology*, 59:461-470 (1996).

Fleming, Tony J., et al., "Negative Regulation of FcεRI-mediated Degranulation by CD81", *J. Exp. Med.*, 186(8) : 1307-1314 (1997).

| Rat CD81-1A12 | F Y D Q A L Q Q A V M X D D |
|---|---|
| |       D        D          D |
| Mouse CD81 | F Y D Q A L Q Q A V M D D D |
| Human CD81 | F Y D Q A L Q Q A V V D D D |

CALCIUM-INDEPENDENT NEGATIVE REGULATION BY CD81 OF RECEPTOR SIGNALLING

RELATED APPLICATIONS

This application is a continuation of application Ser. No. 08/954,279, filed Oct. 20, 1997 (issued as U.S. Pat. No. 6,423,501 on Jul. 23, 2002), which claims the benefit of U.S. Provisional Application Ser. No. 60/032,963, filed Dec. 13, 1996. The entire teachings of the above applications are incorporated herein by reference.

GOVERNMENT FUNDING

Work described herein was funded by grant 1-RO1-GN53950-01 from the National Institutes of Health. The U.S. Government has certain rights in the invention.

BACKGROUND OF THE INVENTION

In the past two decades, tremendous advances have been made in understanding the molecular mechanisms used by various types of cell surface receptors to transduce signals. Nearly all of these advances have come from the study of model systems where a receptor "activates" cells to generate a well-defined response. As knowledge about activating model systems has increased, it has become clear that there are many situations in which the activating signal sent from one receptor is modulated as the direct result of a negative or inhibitory signal sent by another cell surface receptor. While the study of this type of signaling is generally in its infancy, several recent studies have begun to shed light on the molecular mechanisms which underlie receptor-mediated inhibitory signals in immunologic systems. Given the tendency of nature to utilize signaling functions modularly in a variety of signaling pathways, the paradigms outlined by these systems may have implications for the study of inhibitory or deactivating signals in non-immunologic situations as well. In addition, the study of these signals may add new dimensions to the understanding of other widely utilized signaling pathways.

SUMMARY OF THE INVENTION

As described herein, monoclonal antibodies (mAbs) have been isolated which inhibit FcεRI-induced mast cell degranulation. Through protein isolation, peptide sequencing, cloning, and gene expression, CD81 has been identified as a novel inhibitory receptor for FcεRI and FcγRIII. Anti-CD81 mAbs also inhibited passive cutaneous anaphylaxis (PCA) reactions, a model of IgE-dependent, mast cell activation in vivo.

The invention pertains to a method of inhibiting cell surface receptor-mediated signaling comprising contacting a cell with an agent which induces CD81-mediated signal transduction. In a particular embodiment, the cell surface receptor is selected from the group consisting of FcεRI and FcγRIII. In one embodiment, the method is a calcium independent method.

The invention also relates to a method of inhibiting degranulation comprising contacting a cell with an agent which induces CD81-mediated signal transduction. In one embodiment, degranulation is mediated by the FcεRI receptor. In another embodiment, the method is a calcium independent method.

The invention further relates to a calcium independent method of inhibiting cell surface receptor-mediated signaling in a mammal, such as a human, comprising administering to the mammal an effective amount of an agent which induces CD81-mediated signal transduction. In one embodiment, the cell surface receptor is selected from the group consisting of FcεRI and FcγRIII.

The invention also pertains to a method, e.g., a calcium independent method, of inhibiting degranulation induced by a cell surface receptor-mediated signal in a mammal, such as a human, comprising administering to the mammal an effective amount of an agent which induces CD81-mediated signal transduction.

The invention further pertains to a method of treating (e.g., preventing or reducing the severity of) an allergic condition in a mammal, such as a human, comprising administering to the mammal an effective amount of an agent which induces CD81-mediated signal transduction. In particular embodiments, the allergic condition is asthma, hay fever or atopic eczema.

The invention also relates to a calcium independent method of enhancing cell surface receptor-mediated signaling, e.g., FCεRI-mediated signaling and FcγRIII-mediated signaling, comprising contacting a cell with an agent which inhibits CD81-mediated signal transduction.

The invention also pertains to a calcium-independent method of enhancing degranulation comprising contacting a cell with an agent which inhibits CD81-mediated signal transduction. For example, degranulation can be mediated by the FcεRI receptor. The invention also relates to a calcium independent method of enhancing cell surface receptor-mediated signaling in a mammal comprising administering to the mammal an effective amount of an agent which inhibits CD81-mediated signal transduction.

The invention further relates to an assay for identifying agents which alter CD81-mediated signal transduction, comprising combining a cell bearing CD81 with an agent to be tested, under conditions suitable for CD81-mediated signal transduction, and determining the level of CD81-mediated signal transduction. If the level of CD81-mediated signal transduction is altered relative to a control, the agent alters CD81-mediated signal transduction. In a particular embodiment, the agent is one which enhances or induces CD81-mediated signal transduction.

The invention also relates to an assay for identifying agents which alter calcium independent CD81-mediated regulation of cell surface receptor signaling, comprising combining a cell bearing CD81 and an appropriate cell surface receptor with an agent which alters CD81-mediated signal transduction under conditions suitable for signal transduction by CD81 and the cell surface receptor, and determining the level of cell surface receptor signaling.

If the level of cell surface receptor signaling is altered relative to a control, the agent alters calcium independent CD81-mediated regulation of cell surface receptor signaling.

BRIEF DESCRIPTION OF THE DRAWINGS

FIG. 1A illustrates the surface immunoglobulin receptor (sIg) complex and FcγRIIb1 system. FcγRIIb1 provides a negative feedback signal for soluble immunoglobulin production. FIG. 1B illustrates the negative regulation of cytolytic immune cells by killer cell inhibitory receptors (KIR). FIG. 1C illustrates the negative regulation of T-cell receptor-mediated activation signals by CTLA-4.

FIG. 5 illustrates Ly-C peptide 1A12 sequence (SEQ ID NO:1) and alignment with mouse (SEQ ID NO:2) and human CD81 (SEQ ID NO:3).

FIG. 6A shows stable expression of rat CD81 in CHO cells stained with 1A12 mAb. FIG. 6B shows transient expression of rat CD81 in NIH-3T3 cells infected with M.O.I.=5 of rat CD81 recombinant vaccinia virus and incubated for 6 hours prior to staining with 5D1 mAb.

FIG. 9A shows the effect of anti-CD81 on calcium mobilization of fura-2-loaded RBL-2H3 cells triggered through FcεRI as measured by confocal microscopy. Fluo-3 fluorescence per ml $^3$H measurements were normalized by dividing the average fluorescence intensity (F) occurring during the course of the experiment to the average fluorescence intensity at the beginning of the experiment ($F_0$) and expressed as $F/F_0$. Traces are shown of 10 individual cell (thin lines) together with mean values for these cells (thick lines) and represent typical results obtained from five separate experiments. FIG. 9B shows $^3$H-serotonin release from RBL-2H3 cells prepared as in confocal microscopy measurements except that 3 μCi/ml $^3$H-serotonin was added to cultures. FIG. 9C shows $LTC_4$ measurements from $10^6$ anti-DNP IgE saturated RBL-2H3 treated with 1 μg 5D1 (open squares) or buffer (open circles) prior to triggering with 30 ng/ml DNP-HSA for the indicated periods of time.

DETAILED DESCRIPTION OF THE INVENTION

Figure 1A:
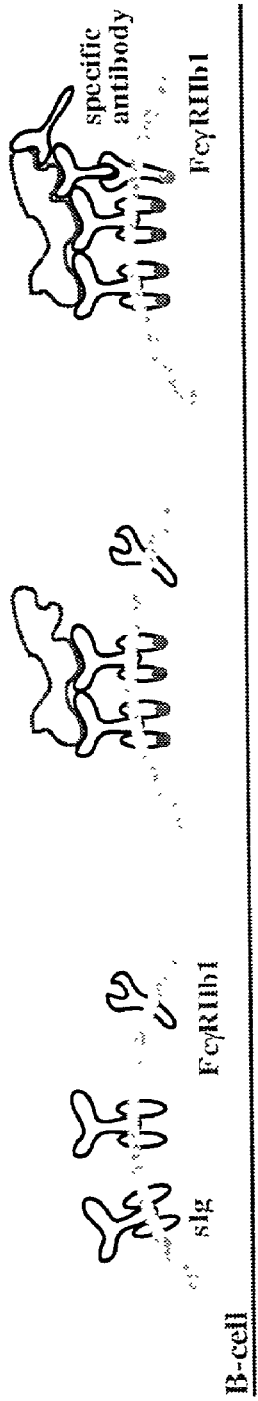
FIGS. 1A–1C illustrate representative immunologic inhibitory signaling systems. Solid dots on sIg, FcγRIII and TCR indicate tyrosine phosphorylation of activating motifs in the cytoplasmic tails of each activating receptor (FIGS. 1A–1C, respectively). Solid dots on FcγRIIB, KIR and CTLA-4 indicate tyrosine phosphorylation of inhibitory motifs in the cytoplasmic tails of each inhibitory receptor (FIGS. 1A–1C, respectively).

Mast cells are important effector cells in IgE-dependent immune responses and allergic diseases (Galli, New. Engl. J. Med., 328:257–265 (1993)), and mast cells also contribute to host defense against parasites and bacteria (Echtenacher et al., Nature 381:75–77 (1996); Galli and Wershil, Nature, 381:21–22 (1996)). Cross-linking of FcεRI-IgE complexes on mast cells and basophils by multivalent antigen initiates a signaling cascade characterized by tyrosine kinase activation, calcium release and influx and, later, by degranulation and release of inflammatory mediators (Jouvin et al., J. Biol. Chem., 269:5918–5925 (1994); Penhallow et al., J. Biol. Chem., 270:23362–23365 (1995); Scharenberg et al., EMBO J., 14:3385–3394 (1995); Lin et al., Cell, 85:985–995 (1996); and (Paul et al., Adv. Immunol., 53:1–29 (1993)).

Like the B and T cell antigen receptors, FcεRI lacks endogenous signaling capacity and utilizes tyrosine phosphorylation to recruit signaling effector molecules. Receptor aggregation leads to phosphorylation and/or activation of several protein tyrosine kinases (PTKs) Lyn, Syk, Btk, Itk, Fer, and FAK (Jouvin et al., J. Biol. Chem., 269:5918–5925 (1994); Penhallow et al., J. Biol. Chem., 270:23362–23365 (1995); Scharenberg et al., EMBO J., 14:3385–3394 (1995); and Kawakami et al., Mol. Cell. Biol., 14:5108–5113 (1994); Kawakami et al., J. Immunol., 155:3556–3562 (1995); and Hamawy et al., J. Biol. Chem., 268:6851–6854 (1993)), as well as protein kinase C isoenzymes (Ozawa et al., J. Biol. Chem., 268:1749–1756 (1993)), MAP kinase (Hirasawa et al., J. Biol. Chem., 270:10960–10967 (1995)), and other signaling molecules such as Cbl and Shc (Ota et al., J. Exp. Med., 184:1713–1723 (1996); and Jabril-Cuenod et al., J. Biol. Chem., 271:16268–16272 (1996)).

The precise role of many of these proteins in degranulation remains undefined. However, it is clear that FcεRI-mediated calcium mobilization, degranulation, and leukotriene and cytokine synthesis depend on early tyrosine kinase activation events, especially the activation of the PTK Syk. FcεRI signaling is initiated by tyrosine phosphorylation of immunoreceptor tyrosine-based activation motifs (ITAM; defined by the sequence $(D/E)x_xYx_2Lx_{6-7}Yx_2(L/I)$ (Flaswinkel et al., Semin. Immunol., 7:21–27 (1995)). Phosphorylated ITAMs (pITAMs) facilitate binding of SH2- domain-containing proteins to FcεRI (Johnson et al., *J. Immunol.*, 155:4596–4603 (1995); Kimura et al., *J. Biol. Chem.*, 271:27962–27968 (1996)).

In addition to activation events, receptor-activated PTKs initiate the regulation of antigen receptor signaling by phosphorylating tyrosine-based motifs on membrane receptors known as inhibitory receptors (Scharenberg and Kinet, *Cell*, 87:961–964 (1996); Cambier, *Proc. Natl. Acad. Sci. USA*, 94:5993–5995 (1997)). These proteins bind SH2-domain-containing phosphatases, the tyrosine phosphatases SHP-1 and SHP-2 and the phosphatidylinositol (Scharenberg et al., *EMBO J.*, 14:3385–3394 (1995); Lin et al., *Cell*, 85:985–995 (1996); Paul et al., *Adv. Immunol.*, 53:1–29 (1993)) 5' phosphatase SHIP, upon co-engagement with antigen or growth factor receptors. Although the molecular targets are still being defined, phosphatase recruitment to inhibitory receptors has one of two general effects on signaling. Engagement of inhibitory receptors that preferentially bind SHIP, such as the low affinity receptor for IgG (FcγRIIb1) (Ono et al., *Nature*, 383:263–266 (1996)), results in selective inhibition of calcium influx with little or no effect on receptor-mediated calcium release or tyrosine phosphorylation. On the other hand, killer cell inhibitory receptors (KIR) bind SHP-1 upon receptor costimulation, resulting in reduced tyrosine phosphorylation, calcium release from the ER, and calcium influx (Burshtyn et al., *Immunity* 4:77–85 (1996); Binstadt et al., *Immunity*, 5:629–638 (1996)). In both mechanisms, calcium mobilization is inhibited along with downstream signaling events.

Figure 1B:
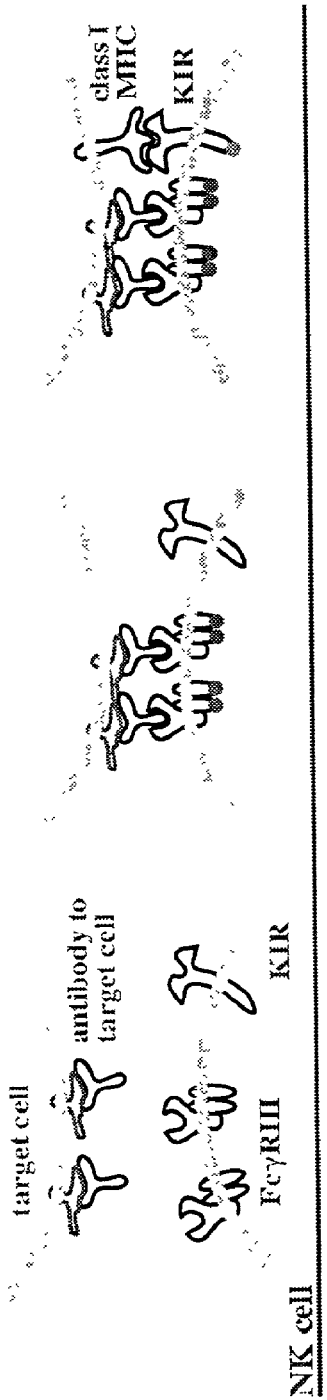
Figure 1C:
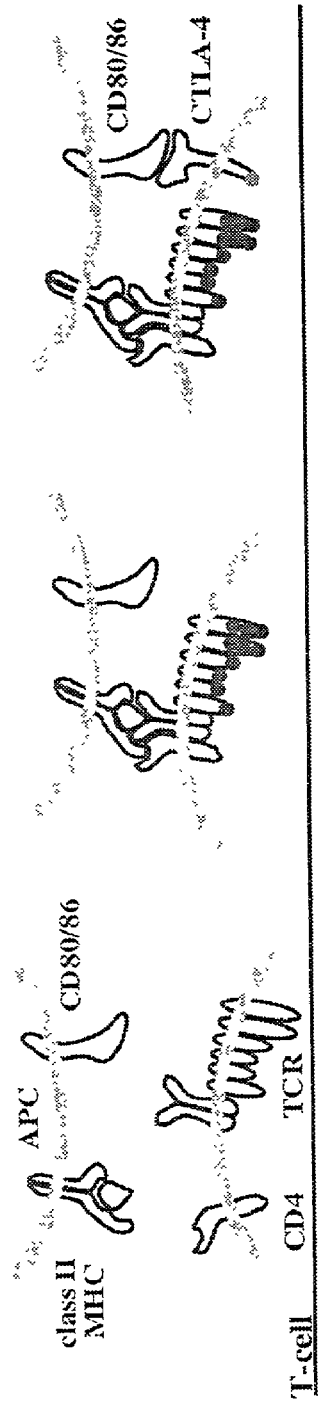
Figure 2:
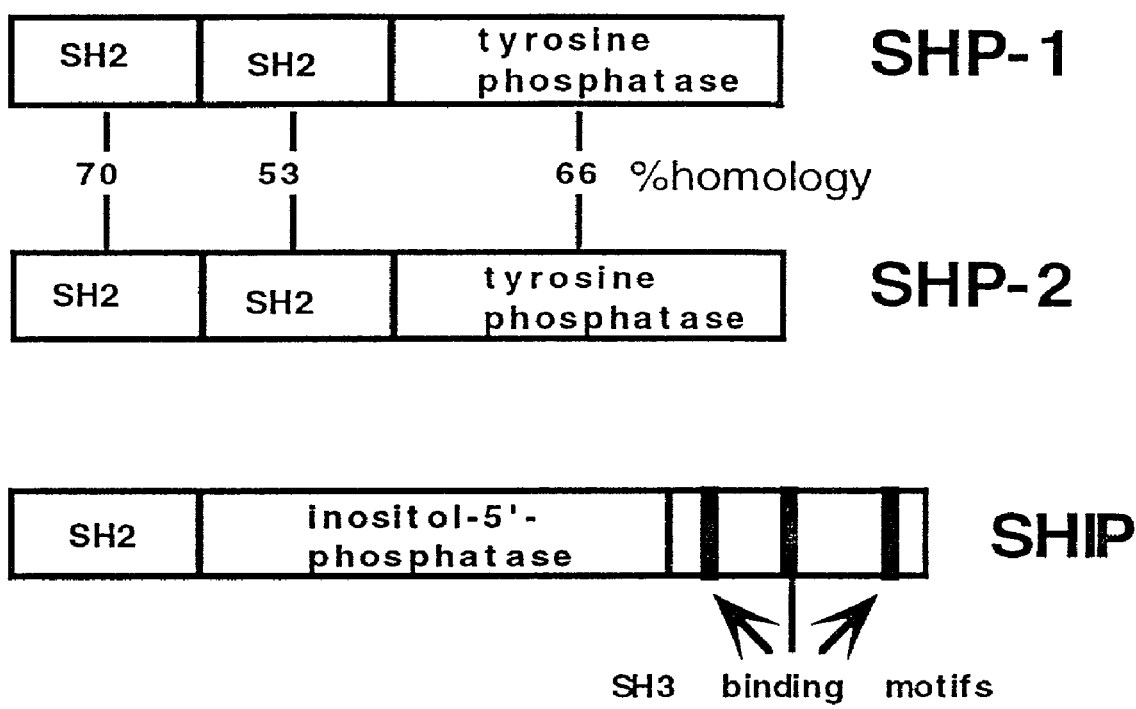
FIG. 2 illustrates the schematic structures of SHP1, SHP2 and SHIP.

Descriptions of three representative systems utilized in recent studies are useful for understanding the nature of inhibitory signals, and are outlined in FIGS. 1A–1C. Briefly, the surface immunoglobulin receptor (sIg) complex and FcγRIIb1 (a low affinity receptor for IgG) are both normally present on B-cell surfaces (FIG. 1A, left panel). When sIg receptors are clustered as a result of contact with antigen (FIG. 1A, middle panel), they typically produce a cell activation signal which induces B-cell proliferation. However, if the same B-cells are stimulated so that the sIg receptors are co-clustered with FcγRIIb1 receptors (for example by contact of the B-cell with an immune complex of cognate antigen and IgG, FIG. 1A, right panel), B-cells fail to proliferate and in some cases may apoptose.

In the natural killer (NK) cell system, a number of cell surface receptors are able to initiate NK cell cytolysis, one of which is FcγRIII (FIG. 1B, left panel). When an NK cell encounters a target cell, it recognizes and kills the target cell if the target cell lacks class I MHC molecules. One of the ways in which NK cells recognize target cells is by binding of IgG bound to the target cell surface to FcγRIII on NK-cells (FIG. 1B, middle panel). If the target cells express appropriate class I MHC molecules which can be recognized by appropriate killer cell inhibitory receptors (KIR) on the NK cell, they are protected from cytolysis (FIG. 1C, right panel).

In the T-cell system, the T-cell antigen receptor (TCR) and CD4 and/or CD8 co-receptors are normally expressed on the surface of resting T-cells (FIG. 1C, left panel). T-cells are activated when their T-cell antigen receptor complexes (TCR's) interact with specific peptide/MHC class II complexes on antigen presenting cells (APCs), resulting in co-clustering of the TCR and CD4 or CD8 (FIG. 1C, middle panel). Upon activation, T-lymphocytes up regulate expression of another surface molecule called CTLA-4, which results in interaction of CTLA-4 with its countereceptors CD80 or CD86 (FIG. 1C, right panel). Since mice which lack CTLA-4 have hyperactivated T-cells and are prone to lymphoproliferative diseases, it is thought that CTLA-4 mediates an inhibitory signal which provides an important negative feedback control for proliferation and cytokine production induced by T-cell receptor activation signals.

While each of these systems is unique in terms of the manner in which the activating and inhibitory signals are engaged, two common features exist among them: 1) Each involves activating signals mediated by homologous cytoplasmic tail motifs known as immunoreceptor tyrosine based activation motifs (ITAMs). These motifs become tyrosine phosphorylated by src family kinases when the activating receptors are engaged by clustering stimuli, resulting in the recruitment to engaged receptors of both src and syk/zap70 family non-receptor tyrosine kinases. Downstream propagation of the activation signal is then mediated by activation of these tyrosine kinases and the resulting phosphorylation of specific substrates. 2) The inhibitory signals are mediated by separate receptors, such as FcγRIIb 1, killer cell inhibitory receptors (KIR), and CTLA-4, which are engaged in concert with the activating receptor when an appropriate stimulus is present. When the inhibitory receptors are appropriately engaged, they become phosphorylated on specific cytoplasmic tail tyrosines by src family kinases, which results in the recruitment of signaling molecules which are inhibitory in function.

Figure 3:
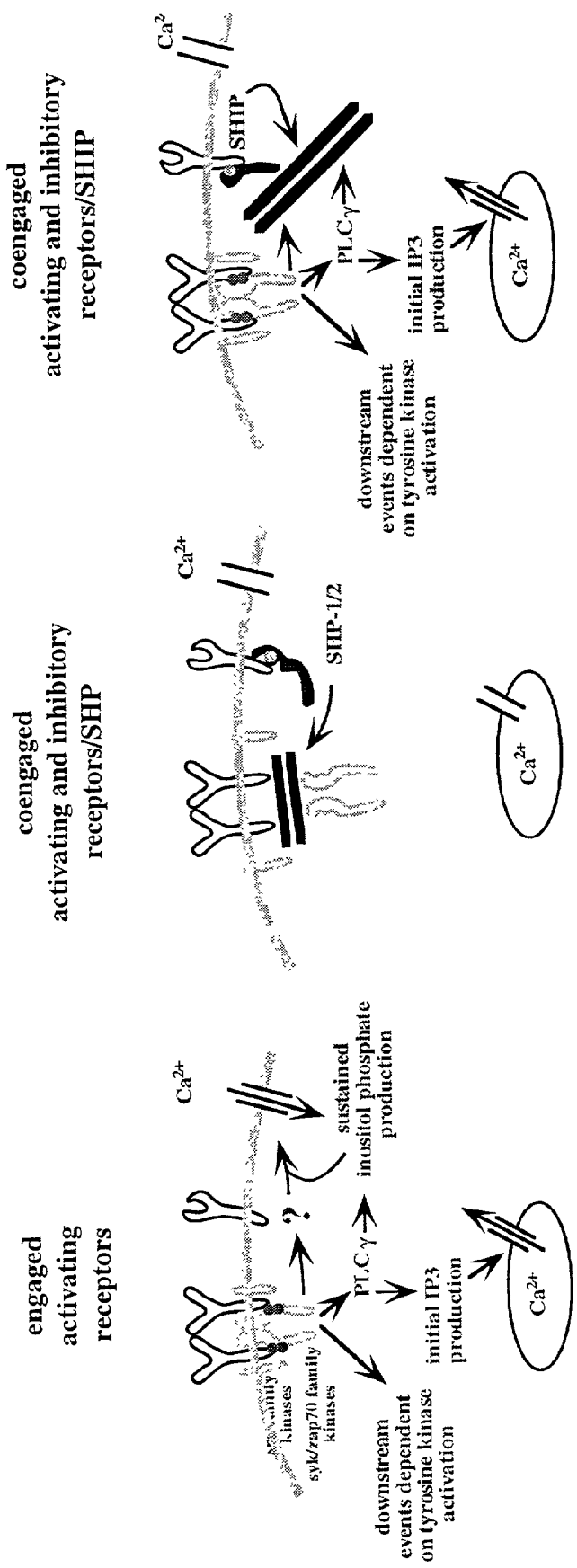
FIG. 3 illustrates the proposed SHP and SHIP inhibitory signaling mechanisms. Solid dots on sIg indicate tyrosine phosphorylation of activating motifs in the cytoplasmic tails of each activating receptor. Solid dots indicate tyrosine phosphorylation of inhibitory motifs in the cytoplasmic tails of each inhibitory receptor.

It appears that SHP-1/SHP-2 and SHIP are recruited for distinct purposes. SHP-1 and SHP-2 attenuate or completely block tyrosine phosphorylation-mediated signals (FIG. 3, middle panel), while SHIP allows a fall strength tyrosine phosphorylation signal to proceed while blocking any downstream events which require sustained elevations of soluble inositol phosphates and/or intracellular calcium (FIG. 3, right panel). One potential explanation can be rationalized by comparing the function of the inhibitory signals mediated by FcγRIIb1 on B-cells and KIR on NK cells. The sIg receptor activating signal serves to notify B-cells that specific antigen is present, and so initiate B-cell maturation and proliferation for the purpose of specific immunoglobulin production. However, co-engagement of sIg and FcγRIIb1 blocks proliferation and can induce apoptosis of the B-cell and a consequent decrease in production of specific immunoglobulin, thereby acting as a negative feedback mechanism. Thus, it appears that the persistence of a full strength tyrosine phosphorylation signal in the absence of sustained inositol phosphate and/or intracellular calcium levels is for the purpose of notifying the B-cell that adequate specific antibody has been produced, and may be the signal which induces apoptosis of that B-cell in the appropriate context.

This situation is subtly, but importantly, different than that of an NK cell. NK cells function by undergoing target cell recognition events mediated by activating receptors which are capable of initiating cytolysis, and the KIR inhibitory signal is required to block inappropriate cytolysis of cells which are recognized but which also bear appropriate class I MHC. Since there would be little utility in the NK cell "knowing" about contact with each and every protected target, an inhibitory mechanism where the activating signal is completely abrogated would seem to be most appropriate. This would account for the apparently SHP-1 predominant inhibitory signal mediated by KIR. To summarize, these results suggest that primarily SHP-1/SHP-2 mediated block would be utilized when the cell has no need to know about the presence of a particular stimulus, while a primarily SHIP-mediated block would be utilized when the cell needs to know and to respond in some altered manner.

IgE-dependent activation of mast cells primarily occurs through antigen-mediated cross-linking of IgE-FcεRI complexes which initiates a signaling cascade ultimately leading to release of proinflammatory mediators (Scharenberg and Kinet, *Chem. Immunol.* 61:72–87 (1995)). FcεRI is a member of the multi-subunit, antigen receptor family which includes B and T cell receptors (BCR and TCR) and receptors for the Fc portions of IgA and IgG (Ravetch and Kinet, *Ann. Rev. Immunol.* 9:457–492 (1991)). These receptors share common features of immunoglobulin-like ligand binding subunit(s) and associated signaling polypeptides which lack endogenous enzymatic activity.

In mast cells, both FcεRI and FcγRIII are expressed as αβγ$_2$ tetramers in which the respective β and FcRγ signaling chains are identical and the ligand-binding α chains are different. In FcεRI, the high affinity IgE binding domain is localized to the FcεRIα subunit (Blank et al., *J. Biol. Chem.*, 266:2639–2646 (1991)) and IgE binding to FcεRIα itself does not contribute to signaling. The FcεRIβ chain and the FcRg homodimer are the signaling components of the FcεRI (αβγ2) tetrameric receptor. Both FcεRIβ and FcRγ have one copy per chain of the immunoreceptor tyrosine-based activation motif (ITAM; Flaswinkel et al., *Semin. Immunol.*, 7:21–27 (1995), Cambier, *J. Immunol.*, 155: 3281–3285 (1995)) defined by the sequence Yx2Lx6-7Yx2L/I.

FcεRI signaling is an aggregation-dependent phenomenon in which multivalent antigen cross-linking of IgE-FcεRI complexes initiates a signaling cascade ITAM tyrosine phosphorylation by src family kinases (Shaw et al., *Semin. Immunol.*, 7:13–20 (1995)). Signaling through FcεRI is characterized initially by tyrosine phosphorylation of FcεRIβ and FcRγ ITAMs by the β-associated src family kinase lyn (Jouvin et al., *J. Biol. Chem.*, 269:5918–5925 (1994)). The lyn-phosphorylated ITAM (pITAM) interaction results in lyn activation. Direct binding of lyn to fusion proteins containing the FcεRIβ, but not the FcRγ ITAM, has been demonstrated (Jouvin et al., *J. Biol. Chem.*, 269: 5918–5925 (1994)). pITAM peptides have been shown to induce lyn phosphorylation both in permeabilized cells and in vitro (Johnson et al., *J. Immunol.*, 155:4596–4603 (1995)).

Following lyn activation, syk is recruited to FcRγ pITAMs via its SH2 domains where it is phosphorylated and activated (Scharenberg and Kinet, *Chem. Immunol.*, 61:72–87 (1995); Jouvin et al., *J. Biol. Chem.*, 269:5918–5925 (1994)). FcRγ pITAM peptides were much more effective than FcεRIβ pITAM peptides at activating syk in vitro in unstimulated RBL-2H3 lysates (Shiue et al., *J. Biol. Chem.*, 270:10498–10502 (1995)). Activated lyn and syk phosphorylate a number of intracellular substrates including PLCγ1, BTK, ITK and cbl (Rawlings et al., *Science*, 271:822–825 (1996); Kawakami et al., *J. Immunol.*, 155:3556–3562 (1995)). Following initial tyrosine kinase activation events, FcεRI signaling, like that of other antigen receptors, involves calcium release from the endoplasmic reticulum (tyrosine kinase-dependent) and a calcium influx, both of which precede degranulation and the release of preformed mediators by granule fusion with the cytoplasmic membrane. An interesting difference between FcεRI and other antigen receptors is that calcium mobilization through FcεRI appears to utilize sphingosine kinase and sphingosine-1-phosphate (S-1-P) (Choi et al., *Nature*, 380:634–636 (1996)) as opposed to the classical phospholipase C/InsP3 pathway.

The rat basophilic leukemia cell line, RBL-2H3, has been widely employed as a model cell in the study of FcεRI-mediated activation. There have been a few reports of monoclonal antibodies (mAbs) directed to membrane components in which co-ligation inhibits FcεRI-mediated degranulation in mast cells. The best characterized examples are MAFA (mast cell function-associated antigen) (Guthmann et al., *Proc. Natl. Acad. Sci. USA*, 92:9397–9401 (1995)) and gp49b1 (Katz et al., *Proc. Natl. Acad. Sci. USA*, 93:10809–10814 (1996)). MAFA is an Mr 20 kd C-type lectin expressed in RBL-2H3 cells both as a monomer and disulphide-linked homodimer that inhibits degranulation by acting upstream of FcεRI-mediated activation of phospholipase Cg1 activation by tyrosine kinases (Guthmann et al., *Proc. Natl. Acad. Sci. USA*, 92:9397–9401 (1995)).

The target of gp49B1 is less well defined; however it appears to act via a tyrosine-based ITIM (immunoreceptor tyrosine-based inhibitory motif) defined by the sequence V/Ix2Yx2I/L utilized by the NK inhibitory receptor (KIR), CD22, CTLA-4, and FcγRIIβ1. Tyrosine phosphorylation of the ITIM in KIR induces binding of the SHP-1 tyrosine phosphatase. SHP-1 recruitment is intimately associated with inhibition of calcium influx and mobilization presumably enacted through yet-to-defined dephosphorylation events. Over expression of phosphatase-inactive SHP-1 ablates the inhibitory activity of endogenous SHP-1. ITIM-mediated recruitment is not restricted to SHP-1, as a second SH2-containing phosphatase (SHP-2) is utilized by CTLA-4, and the FcgRIIb1 ITIM binds either SHP-1 or the SH2-containing inositol phosphatase (SHIP). In the case of gp49b1, it is unclear which effector is being utilized but it has been demonstrated that a splice variant (gp49A) which lacks the cytoplasmic ITIM but is identical in the extracellular domains lacks detectable inhibitory activity. In addition to MAFA, antibodies to the glycolipid Gd1b and the AD1 antigen (rat homologue of CD63) have also been described to inhibit FcεRI-mediated degranulation in RBL-2H3 cells.

Clustering of the high affinity IgE receptor (FcεRI) by antigen initiates a signaling cascade characterized by tyrosine kinase activation, calcium release and influx and, later, by degranultation and release of inflammatory mediators. In order to examine how FcεRI signaling is negatively regulated, a panel of monoclonal antibodies to mast cell membrane antigens was generated and screened for inhibition of IgE-mediated mast cell degranulation. Two degranulation inhibitory antibodies, designated 1A12 and 5D1, immunoprecipitated a Mr 25 kd protein from surface-iodinated rat basophilic leukemia (RBL-2H3) cells. Lys-C peptide sequence obtained from 1A12-immunoaffinity purified immunoprecipitates was found to be highly homologous to mouse and human CD81. Subsequent cloning and expression of rat CD81 cDNA from RBL-2H3 confirmed that 1A12 and 5D1 recognize rat CD81 and that CD81 cross-linking inhibits FcεRI-mediated mast cell degranulation. Mouse hybridoma 1A12 also known as mouse hybridoma anti-rat CD81: 1A,12, was deposited on Aug. 2, 2005, on behalf of Beth Israel Deaconess Medical Center, Inc., 330 Brookline Avenue, Boston, Mass. 02215, U.S.A., at the American Type Culture Collection, 10801 University Boulevard, Manassas, Va. 20110, U.S.A., under Accession No. PTA-6902. Mouse hybridoma 5D1, also known as mouse hybridoma anti-rat CD81: 5D1, was deposited on Aug. 2, 2005, on behalf of Beth Israel Deaconess Medical Center, Inc., 330 Brookline Avenue, Boston, Mass. 02215, U.S.A., at the American Type Culture Collection, 10801 University Boulevard, Manassas, Va. 20110, U.S.A., under Accession No. PTA-6901.

Signaling through the high affinity receptor for immunoglobulin E (FcεRI) results in the coordinate activation of tyrosine kinases prior to calcium mobilization. Receptors capable of interfering with the signaling of antigen receptors, such as FcεRI, recruit tyrosine and inositol phosphatases that results in diminished calcium mobilization. It is shown herein that antibodies recognizing CD81 inhibit FcεRI-mediated mast cell degranulation but, surprisingly, without affecting aggregation-dependent tyrosine phosphorylation, calcium mobilization, or leukotriene synthesis. Furthermore, CD81 antibodies also inhibit mast cell degranulation in vivo as measured by reduced passive cutaneous anaphylaxis responses. These results reveal an unsuspected calcium-independent pathway of antigen receptor regulation which is accessible to engagement by membrane proteins and on which novel therapeutic approaches to allergic diseases can be based.

CD81 belongs to the transmembrane 4 superfamily (TM4SF) which includes CD9, CD53, CD63 and CD82 (Wright and Tomlinson, *Immunol. Today*, 15:588–594 (1994)). TM4SF proteins have been found to associate with HLA-DR, CD4, CD19/21/Leu-13, small GTP-binding proteins and an unidentified tyrosine phosphatase and (via mAb cross-linking) to induce calcium mobilization and activate syk.

CD81 is broadly expressed on hematopoietic cells (T and B lymphocytes, granulocytes, monocytes) and on some non-lymphoid tumors. The function of CD81 (or other TM4SF proteins) is incompletely understood, although CD81 appears to modulate the signaling of other membrane receptors. CD81 is found in the CD19/CD21 complex on B cells, and mAbs to CD81 or CD19 have been reported to reduce the threshold for B cell receptor signaling (Fearon and Carter, *Annu. Rev. Immunol.*, 13:127–149 (1995)) and enhance B cell adhesion via VLA4 (Behr and Schriever, *J. Exp. Med.*, 182:1191–1199 (1995)). Consistent with a costimulatory role in B cell receptor signaling, CD81 −/− mice express lower levels of CD19 on B cells which is proposed to contribute to a defect in humoral immunity (Maecker and Levy, *J. Exp. Med.*, 185:1505–1510 (1997)). For T lineage cells, both stimulatory and inhibitory activities for anti-CD81 mAbs have been reported (Secrist et al., *Eur. J. Immunol.*, 26:1435–1442 (1996); Todd et al., *J. Exp. Med.*, 184:2055–2060 (1996); Oren et al., *Mol. Cell. Biol.*, 10:4007–4015 (1990); and Boismenu et al., *Science*, 271: 198–200 (1996)). CD81 ligation enhances IL-4 production from antigen-specific CD4+ T cells (Secrist et al., *Eur. J. Immunol.*, 26:1435–1442 (1996)) and integrin activation and IL 2-dependent proliferation in human thymocytes (Todd et al., *J. Exp. Med.*, 184:2055–2060 (1996)). Alternatively, CD81 was originally called TAPA-1 (target of antiproliferative antibody) based on inhibition of proliferation in human T cell lines by CD81 antibodies (Oren et al., *Mol. Cell. Biol.*, 10:4007–4015 (1990)). Some of these pleiotropic effects may stem from the potential signaling molecules with which CD81 has been reported to associate including CD4, CD8, MHC class II, other TM4SF proteins, integrin VLA4, and phosphatidylinositol 4-kinase (Wright and Tomlinson, *Immunol. Today*, 15:588–594 (1994); Imai et al., *J. Immunol.*, 155:1229–1239 (1995); Angelisova et al., *Immunogenetics*, 39:249–256 (1994); Mannion et al., *J. Immunol.*, 157:2039–2047 (1996); and Berditchevski et al., *J. Biol. Chem.*, 272:2595–2598 (1997)).

Mast cell FcεRI can be saturated with monoclonal IgE antibodies. In the absence of cross-linking by appropriate antigen, IgE binding to FcεRI does not activate mast cells. Monoclonal antibodies are purified from culture supernatants or mouse ascitic fluid (produced by injection of antibody-producing cells into immunocompromised mice by standard techniques, such as those described in Kohler and Milstein, *Nature*, 256:495–497 (1975); Kozbar et al., *Immunology Today*, 4:72 (1983); and Cole et al., *Monoclonal Antibodies and Cancer Therapy*, Alan R. Liss, Inc., pp. 77–96 (1985)). Cross-linking by the antigen (protein binding to the IgE) normally induces cell degranulation which can be quantitated by enzyme assay or radioactivity release assay. Antibody treatment of CD81 mast cells inhibits IgE-mediated degranulation; 20 ng of 5D1 monoclonal antibody per $10^5$ RBL-2H3 cells inhibits degranulation through IgE-mediated channels by greater than 75%.

Mast cells are a major cell in allergic reactions. Thus, the present invention can be used to develop agents, e.g., antibodies, which inhibit the allergic process, as well as to develop compounds for the treatment of allergies, anaphylactic reactions and related diseases. Agents can also be developed which mimic the process of CD81-mediated inhibition of mast cell degranulation. Anti-CD81 antibodies are more inhibitory than antibodies to other different proteins for IgE-mediated degranulation, particularly because anti-CD81 antibodies act directly and do not require secondary reagents. The work described herein can also be used to develop model systems for the study of activation of mast cells through the FcεRI receptor and to improve the therapeutic capability to modulate the function of these cells.

Agents described herein can be anything which binds to or interacts with CD81 and induces (i.e., activates) or enhances CD81-mediated signal transduction. For example, the agent can be a small molecule, a peptide, or a polyclonal or monoclonal antibody, such as an anti-CD81 antibody. In particular embodiments, the antibody is 5D1 or 1A12.

Figure 7A:
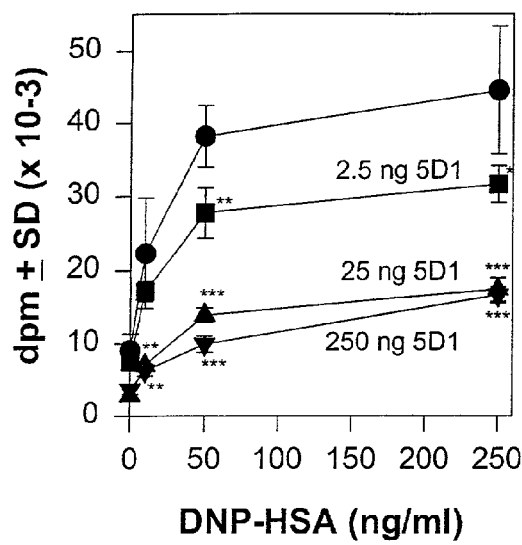
FIGS. 7A–7D are graphs of the effect of preincubation of purified mAb 5D1 on FcεRI-mediated degranulation in RBL-2H3 cells. Data shown indicate the results of degranulation of IgE-saturated RBL-2H3 cells after incubation with buffer (filled circles) or purified 5D1 mAb at 2.5 ng (filled squares), 25 ng (filled triangles), or 250 ng (filled inverted triangles) (FIGS. 7A, 7C, 7D) or with 100 ng (7B) of 5D1 mAb per $10^5$ cells prior to triggering with the indicated concentrations of DNP-HSA (FIG. 7A), 50 ng/ml DNP-HSA (FIGS. 7C and 7D) or with PMA and ionomycin (FIG. 7B). Data are expressed as mean dpm±standard deviation or as percentages of control (no antibody) mean dpm. Statistical significance versus untreated controls was determined using an unpaired Student's t-test: *, $p<0.05$; , $p<0.01$; *, $p<0.001$ for FIG. 8A. All data points in FIGS. 8B and 8D were found to be significantly different from controls ($p<0.02$) with the exception of the 5 minute preincubation time point with 2.5 ng mAb 5D1 (FIG. 8C, $p=0.067$).
Figure 7B:
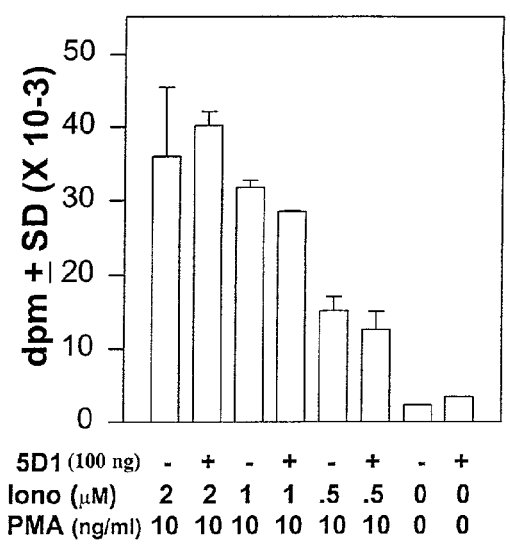
Figure 7C:
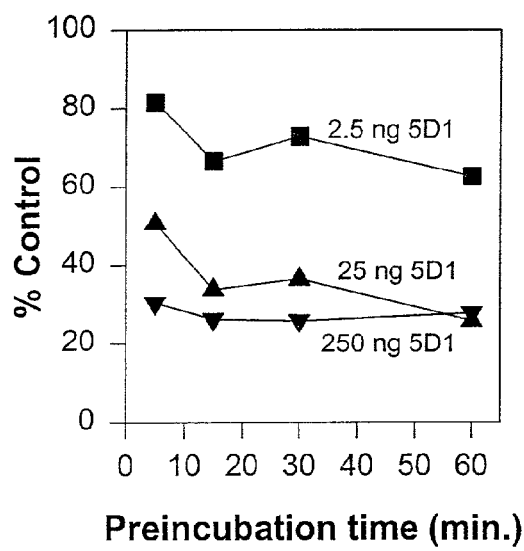
Figure 7D:
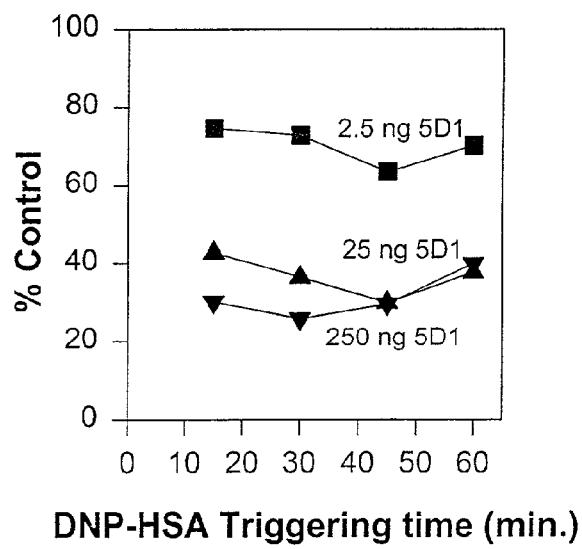

In order to identify membrane proteins capable of regulating FcεRI signaling, mAbs to the rat basophilic leukemia (RBL-2H3) cell line were produced and antibodies which inhibited FcεRI-mediated degranulation were identified. The results are shown in FIGS. 7A–7D. Cells were preincubated with mAb 5D1 or buffer for 30 minutes (FIGS. 7A, 7B, 7D) or for the indicated times (FIG. 7C) at room temperature prior to triggering for 30 minutes (FIGS. 7A–7C) or as indicated (FIG. 7D). The data shown are representative of more than 10 experiments with the 5D1 mAb. As shown in FIG. 7A, pretreatment of anti-DNP IgE-saturated RBL-2H3 cells with purified mAb 5D1 inhibited FcεRI-mediated degranulation by 75% as measured by release of granule-stored $^3$H-serotonin. Blockage of serotonin release was significant (*, $p<0.05$) even at subsaturating concentrations of 5D1 (2.5 nm mAb/$10^5$ cells, FIG. 7A). 5D1-mediated inhibition was specific for FcεRI signaling, as degranulation induced by phorbol myristate acetate (PMA) and calcium ionophore ionomycin were unaffected (FIG. 7B). Furthermore, maximal inhibition of FcεRI-mediated degranulation by mAb 5D1 required only brief periods of preincubation (FIG. 7C), and inhibition was sustained for at least one hour of antigen stimulation (FIG. 7D).

Figure 8:
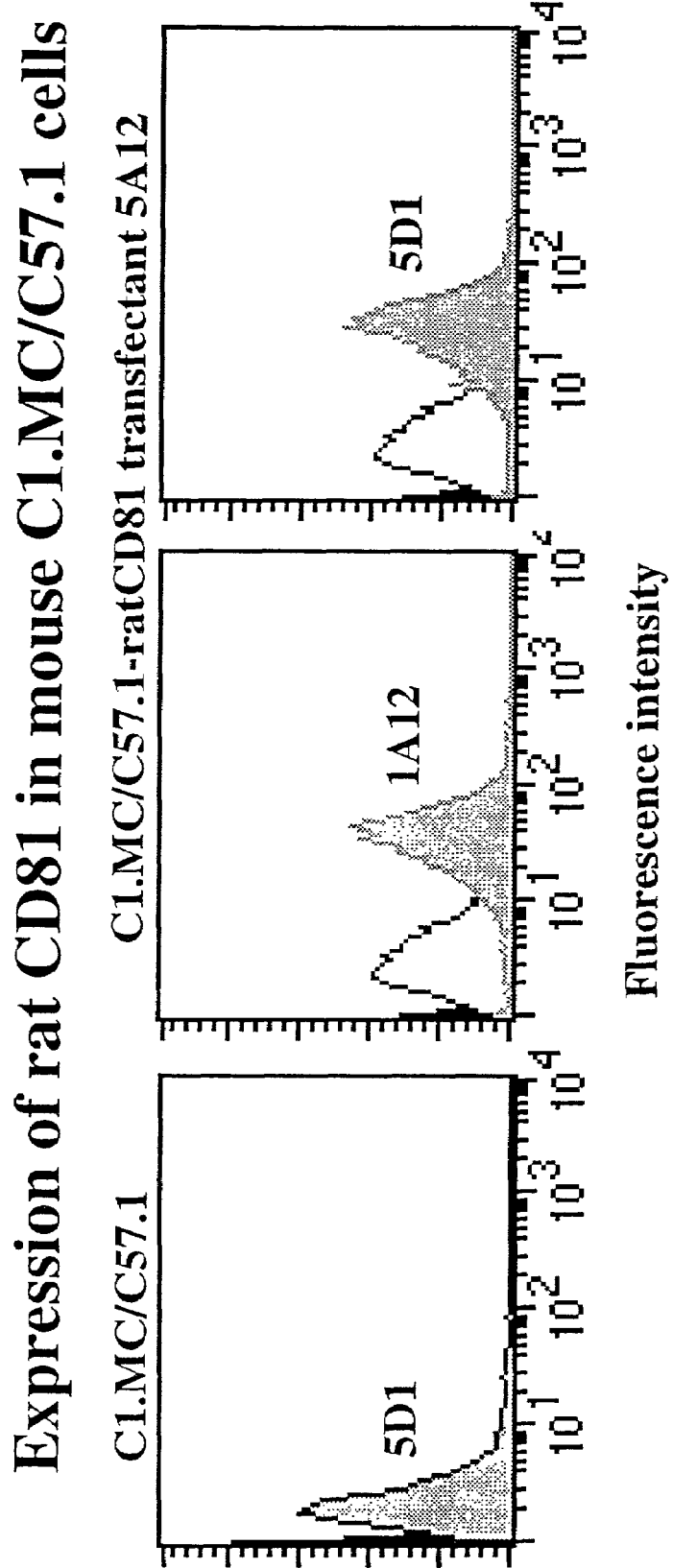
FIG. 8 shows expression of rat CD81 in mouse mast cell line C1.MC/C57.1 by FACS staining with 5D1 and 1A12 mAbs.

The protein recognized by the degranulation-inhibitory 5D1 mAb was then identified. 5D1 and a second degranulation-inhibitory mAb (1A12) recognized proteins of Mr 25 kDa. 5D1 and 1A12 blocked each others' binding to RBL-2H3 cells, although neither mAb inhibited IgE binding and, conversely saturation of FcεRI with IgE had no effect on 1A12 binding, suggesting that 1A12 and 5D1 recognized the same protein (see FIG. 8) and that FcεRI and the 1A12/5D1 antigen were not co-localized on the cell membrane. Since mAb 1A12 was more effective at immunoprecipitation and on Western blots, it was used for protein purification. Batch preparations of RBL-2H3 extracts were immunoprecipitated with mAb 1A12, resolved on preparative SDS-PAGE and transferred to nitrocellulose for protein sequencing. Peptide sequence obtained from Lys-C digests of 1A12 immunoprecipitates is shown aligned with homologous sequences from mouse and human CD81 in FIG. 5. Based on these data, rat CD81 was cloned from a RBL-2H3 cDNA library using mouse CD81 cDNA as a probe and expressed in the mouse mast cell line C1.MC/C57.1 (Young et al., *Proc. Natl. Acad. Sci. USA* 84:9175–9179 (1987)). FACS profiles of C1.MC/C57.1 transfectants are shown in FIG. 8; both degranulation-inhibitory mAbs 1A12 and 5D1 recognized rat CD81.

To target the site of CD81 inhibition of degranulation, the effect of CD81 antibodies on the earliest events of FcεRI signal transduction, i.e. tyrosine phosphorylation of proteins by activated, non-receptor tyrosine kinases including Lyn and Syk, and calcium mobilization (Jouvin et al., *J. Biol. Chem.*, 269:5918–5925 (1994); Penhallow et al., *J. Biol. Chem.*, 270:23362–23365 (1995); Scharenberg et al., *EMBO J.*, 14:3385–3394 (1995); Lin et al., *Cell*, 85:985–995 (1996)) was examined. In these experiments, IgE-saturated RBL-2H3 cells were pretreated with purified anti-CD81 prior to triggering with DNP-HSA for the indicated periods of time, followed by extraction and immunoprecipitation of total tyrosine-phosphorylated proteins. No major changes in the pattern of FcεRI-induced tyrosine phosphorylation were detected with anti-CD81 treatment prior to antigen triggering. Incubation of RBL-2H3 cells with 5D1 alone (no antigen triggering) did not induce detectable tyrosine phosphorylation.

Figure 9A:
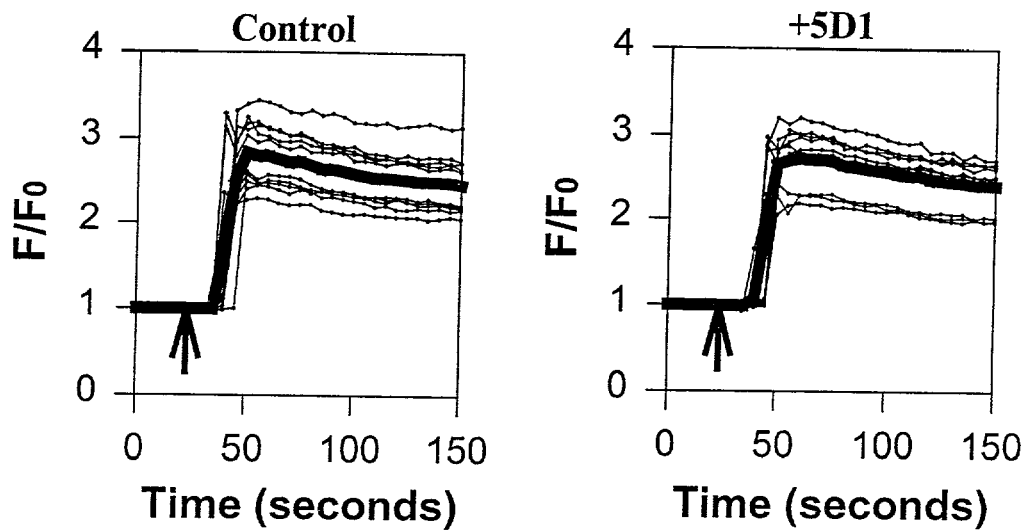
FIGS. 9A–9C are graphs showing that CD81 mAbs fail to inhibit FcεRI-induced tyrosine phosphorylation, calcium mobilization, and leukotriene synthesis.
Figure 9B:
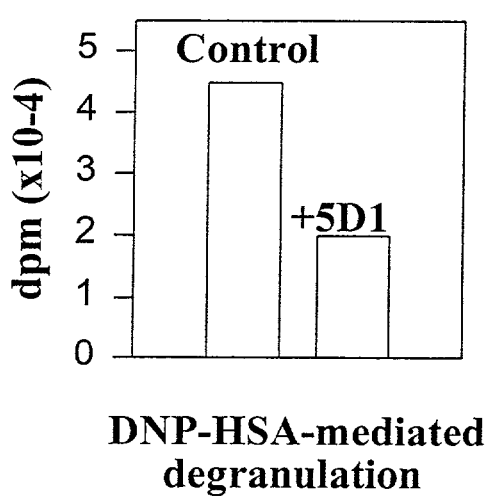
Figure 9C:
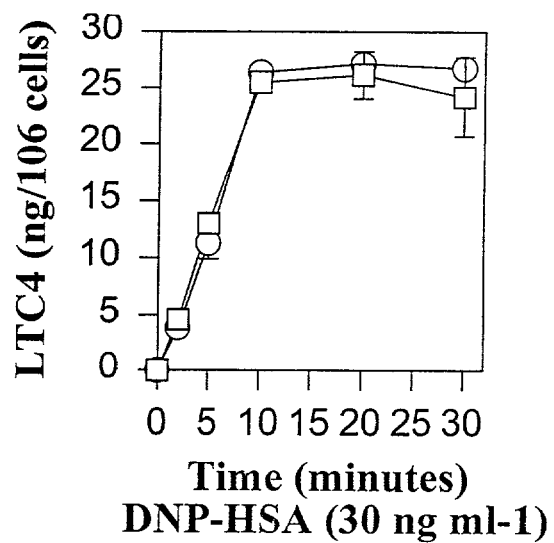

The effect of anti-CD81 on FcεRI-induced calcium mobilization was monitored on individual, adherent RBL-2H3 cells by confocal microscopy in cells loaded with calcium dye fluo-3. As shown in FIG. 9A, no inhibition of FcεRI-induced calcium mobilization in anti-CD81 treated versus controls was observed by confocal microscopy, despite inhibition of degranulation under these conditions (FIG. 9B). Anti-CD81 pretreatment had no effect on calcium release from intracellular stores in cells triggered in $Ca^{2+}$-free buffer containing 0.5 mM EGTA or on pre-triggering baseline values. Similar results were also obtained with RBL-2H3 triggered through FcεRI in suspension using a spectrophotometer. In separate experiments, anti-CD81 mAb 5D1 did not inhibit leukotriene $C_4$ ($LTC_4$) production induced by DNP-HSA/IgE stimulation (FIG. 9C). LTC4 production is dependent on activation of phospholipase A2 (tyrosine kinase and calcium-dependent) and is regulated by PMA-sensitive, protein kinase C isozymes (Currie et al., *Biochem. J.*, 304:923–928 (1994)); Ali et al., *J. Immunol*, 153:776–788 (1994)). These data suggest that CD81 acts independently of early tyrosine phosphorylation and calcium mobilization events which are critical for mast cell degranulation.

These results were unexpected in light of the reported modes of action of other inhibitory receptors. These proteins fall into two major classes; type I, transmembrane proteins that are members of the Ig superfamily (FcγRIIb1, KIR, CTLA-4, CD22, gp49b1, paired Ig-like receptors (PIR), signal-regulatory proteins (SIRPs)) and type II, transmembrane, C-type lectins (e.g. Ly-49, NKG2A, mast cell function associated protein (MAFA)) (Ono et al., *Nature*, 383: 263–266 1996); Burshtyn et al., *Immunity*, 4:77–85 (1996)).

CD81 differs from these inhibitory receptors in three important ways. First, unlike other inhibitory receptors, CD81 inhibits FcεRI-mediated degranulation while leaving both tyrosine phosphorylation and calcium mobilization apparently unaffected. While these results cannot exclude a very selective inhibition of kinase activity by CD81 antibodies, it is clear that no detectable effect is found on tyrosine kinase-sensitive calcium mobilization of $LTC_4$ production. Second, CD81 belongs to a different structural class of proteins than the other inhibitory receptors. CD81 is a TM4SF protein with four transmembrane spanning segments, two extracellular loops, two short cytoplasmic tails, and a short intracellular loop between transmembrane segments 2 and 3 (Wright and Tomlinson, *Immunol. Today*, 15:588–594 (1994)). Third, the cytoplasmic tails of CD81 lack ITIM motifs. While there is an ITIM-like sequence (GCYGAI) in the short intracellular loop between transmembrane segments 2 and 3, there is no evidence that this site is phosphorylated by tyrosine kinases or capable of binding to SH2 domains.

Figure 10A:
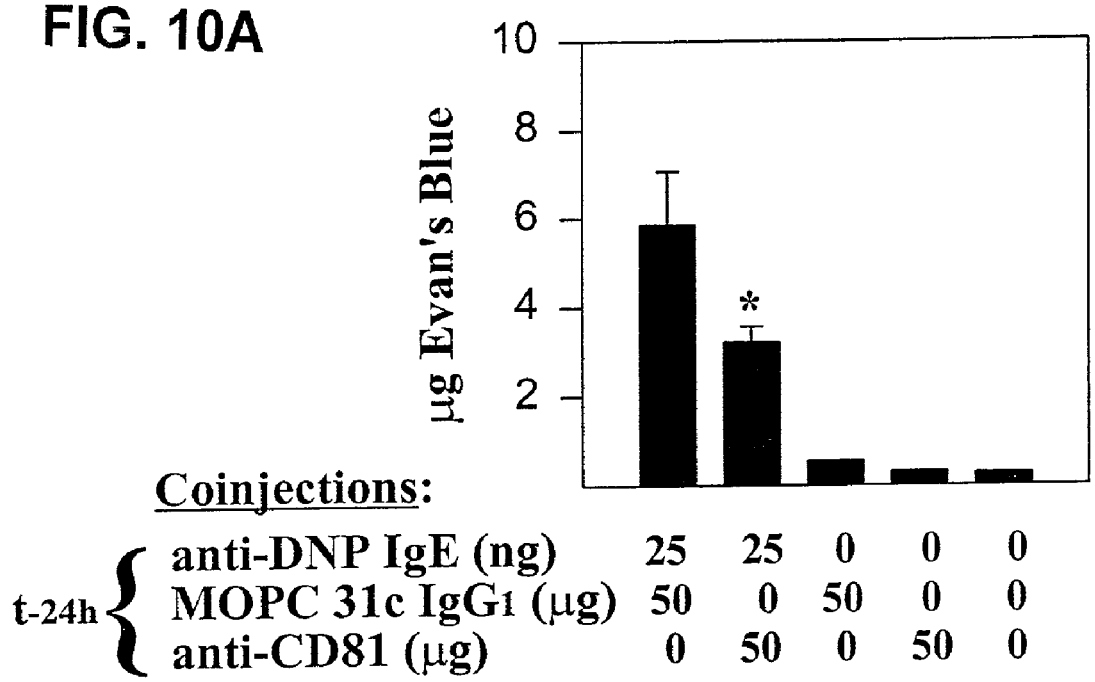
FIG. 10A–10B are graphs showing inhibition of passive cutaneous anaphylaxis in Wistar rats by anti-CD81. Male Wistar rats were injected with (FIG. 10A) 25 ng DNP-specific IgE mixed with 50 μg anti-CD81 mAb 5D1 (mouse IgG1) or control mouse IgG1 mAb (MOPC 31c, specificity unknown) or (FIG. 10B) 100 ng DNP-specific IgE alone. Statistical significance was determined using an unpaired Student's t-test: *, $p<0.05$; **, $p<0.01$ (actual values 10A, $p=0.024$ versus MOPC 31c controls; 10B, $p=0.009$ versus anti-LFA-1β controls).

In order to assess the activity of anti-CD81 in FcεRI signaling in normal mast cells, the passive cutaneous anaphylaxis (PCA) model, a classic system for studying mast cell activation in vivo (Wershil et al., *J. Immunol.*, 154: 1391–1398 (1995); Dombrowicz et al., *J. Clin. Invest.*, 99:915–925 (1997)), was chosen. In these experiments, rats were injected intradermally with IgE mixed with anti-CD81 mAb 5D1 (IgG1) or with class-matched mouse (IgG1) as control (FIG. 10A). Additional rats received anti-DNP IgE alone into the skin at time 0, followed by a second injection (buffer, 5D1, or anti-rat LFA-1β (IgG1)) (FIG. 10B) into IgE-injected sites 21 hours after IgE injections. Twenty four hours after IgE priming, rats received 1 mg of antigen intravenously (DNP-HSA containing 1% Evan's blue dye). Mast cell activation through FcεRI in PCA results in the release of several vasoactive substances which act to increase vascular permeability, a property which is quantified by local accumulation of the Evan's blue dye from the vasculature into the sites of IgE injections. These results are expressed as μg Evan's blue converted from $A_{610}$ measurements of formamide-extracted tissue biopsies (Dombrowicz et al., *J. Clin. Invest.*, 99:915–925 (1997)). As shown in FIG. 10A, coinjection of anti-CD81 mAb 5D1 during IgE priming significantly inhibited IgE-dependent PCA reactions (p=0.024) compared to class-matched controls.

Figure 10B:
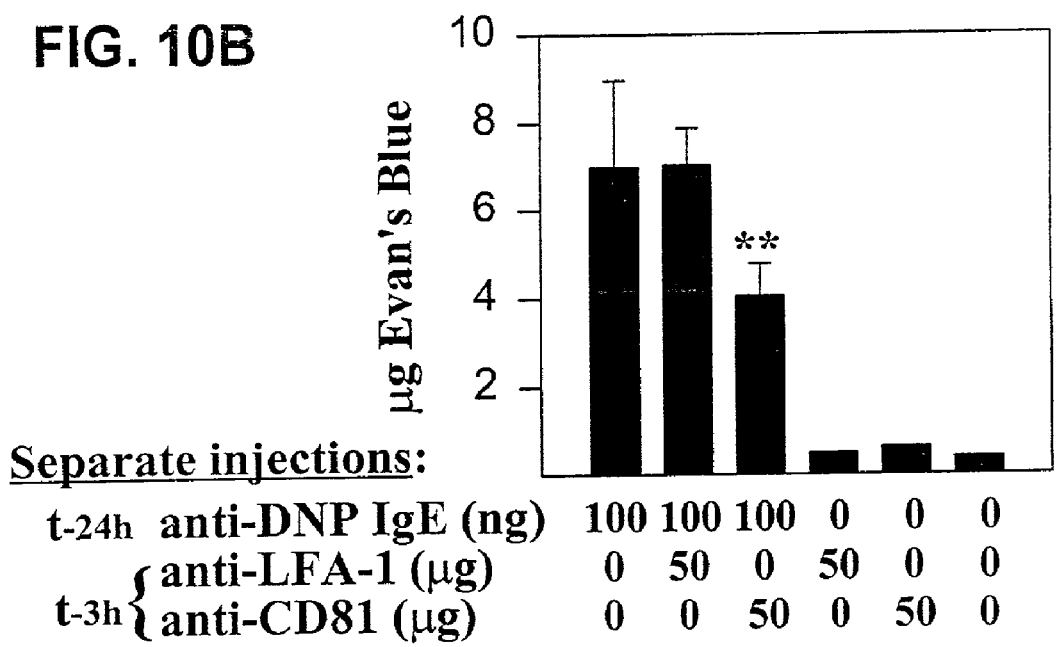

To limit the possibility of non-specific suppression of PCA reactions due to tissue deposition of $IgG_1$ mAbs, these experiments were repeated by injecting anti-CD81 mAb 5D1 or anti-LFA-1β (CD18) into the IgE-injected sites 3 hours before antigen administration. LFA-1β is expressed on mast cell lines including RBL-2H3 but anti-LFA-1β has no effect on FcεRI-mediated degranulation in RBL-2H3 cells (Weber et al., *Scand. J. Immunol.*, 45:471–481 (1997)). Similar to coinjection of IgE and $IgG_1$ mAbs, separate injections of anti-CD81 yielded significant inhibition of PCA reactions compared to anti-LFA-1β controls (FIG. 10B).

Thus, it is demonstrated herein that CD81 is a novel inhibitory receptor for FcεRI. The observation that CD81 acts on calcium-independent events required for mast cell degranulation distinguishes CD81 from previously described inhibitory receptors, such as FcγRIIb1 and KIR, which act upstream of calcium influx. Anti-CD81 mAbs also inhibited IgE-dependent PCA reactions, which suggests the CD81 pathway is present in normal mast cells and capable of being engaged to inhibit mast cell responses in vivo. Therefore, the CD81 inhibitory pathway can be utilized in therapeutic strategies aimed at intervention of allergic responses.

RBL-2H3 cells express FcεRI, CD81 and endogenous rat FcγRIII receptors. However, no high-affinity reagent (antibody) is available to trigger the FcγRIII receptors on RBL-2H3; the 2.4G2 antibody (anti-mouse FcγRII/FcγRIII) was used for this purpose. To demonstrate that CD81 stimulation inhibits degranulation induced through FcγRIII signaling as it does for FcεRI, murine FcγRIIIα chain cDNA was expressed in RBL-2H3 cells.

FcγRIII binding of IgG is detectable only when IgG is present in the form of IgG-containing immune complexes which cross-link FcγRIII receptors and initiate intracellular signals. One of the methods of triggering FcγRIII is through stimulation with crosslinked anti-FcγRIII antibodies. FIG. 12 shows the results when RBL-2H3 and FcγRIII-transfectants of RBL-2H3 were loaded with $^3$H-serotonin in the presence (DNP-HSA stimulation) or absence (immune complex stimulation) of DNP-specific IgE. After overnight incubation, cells were washed and incubated with culture media or media containing 200 ng of anti-rat CD81 mAb 5D1 prior to triggering with optimized concentrations of DNP-HSA or with preformed immune complexes of 2.4G2/anti-rat IgG F(ab')$_2$. Degranulation was allowed to proceed for 30 minutes at 37° C. and released $^3$H-serotonin was quantitated by scintillation counting. As shown in FIG. 12, DNP-HSA induces IgE-mediated degranulation in all four cell lines which is inhibitable by anti-CD81 mAb 5D1. 2.4G2/anti-rat IgG F(ab')2 preformed complexes, but not anti-rat IgG F(ab)2 alone, induce degranulation only in cells expressing mFcγRIII receptors (RBL-2H3 transfectants A10, D10 and H11), a process which is also inhibitable by preincubation with 5D1. This data provides the identification of CD81 as a common inhibitor of both FcεRI and FcγRIII.

Accordingly, the present invention relates to a method of inhibiting or enhancing cell surface receptor signaling, e.g., FcεRI-mediated or FcγRIII-mediated signaling. The method of inhibiting cell surface receptor signaling comprises contacting a cell with an effective amount of an agent which enhances or induces CD81-mediated signal transduction. Alternatively, the method can be a method of inhibiting cell surface receptor signaling in a mammal, comprising administering to the mammal an effective amount of an agent which enhances or induces CD81-mediated signal transduction. Appropriate cells are any cell type which expresses or has been designed to express (e.g., by transfection or genetic engineering) both CD81 and a suitable cell surface receptor.

For example, inhibition of the cell surface receptor signals which induce mast cell degranulation is useful in methods of treating allergic conditions or inflammatory disorders. Enhancement of the cell surface receptors which induce mast cell degranulation is useful in inducing an inflammatory response, for example, in response to bacterial or parasite infection.

The method of enhancing cell surface receptor signaling comprises contacting a cell with an effective amount of an agent which inhibits or prevents CD81-mediated signal transduction. Alternatively, the method can be a method of enhancing cell surface receptor signaling in a mammal, comprising administering to the mammal an effective amount of an agent which inhibits or prevents CD81-mediated signal transduction. It may be clinically beneficial to enhance cell surface receptor signaling in a mammal, or the functional results thereof, such as degranulation, in conditions where an inflammatory response and/or release of leukotrienes and cytokines is beneficial, such as in host defense against parasites and bacteria.

The invention also pertains to a method of treating an allergy (e.g., asthma, hay fever or atopic eczema) or inflammatory condition in a mammal comprising administering to the mammal an effective amount of an agent which induces CD81-mediated signal transduction. For example, the method can be used to treat allergic or inflammatory responses associated with disorders such as autoimmune (Type I) diabetes mellitus, rheumatoid arthritis, ankylosing spondylitis, sarcoidosis, Sjögren's syndrome, multiple sclerosis, inflammatory bowel disease (i.e., Crohn's disease and ulcerative colitis), dermatomyositis, scleroderma, polymyositis, systemic lupus erythematosus, biliary cirrhosis, autoimmune thyroiditis, and autoimmune hepatitis, as well as many dermatological disorders, including psoriasis, contact sensitivity and atopic dermatitis.

As used herein, "inhibit" is intended to encompass any qualitative or quantitative reduction in a measured effect or characteristic, including complete prevention, relative to a control. As also used herein, "enhance" is intended to encompass any qualitative or quantitative increase in a measured effect or characteristic relative to a control. An "effective amount" of a given agent is intended to mean an amount sufficient to achieve the desired effect, e.g., the desired therapeutic effect, under the conditions of administration, such as an amount sufficient for inhibition or enhancement of CD81-mediated signal transduction.

The present invention also relates to preparations for use in the inhibition or enhancement of cell surface receptor signaling, and the treatment of allergic diseases and inflammatory disorders, the preparation including an inhibitor or promoter of CD81-mediated signal transduction, together with a physiologically acceptable carrier and optionally other physiologically acceptable adjuvants.

According to the method, a therapeutically effective amount of one or more agents (e.g., a preparation comprising an inhibitor or promoter of CD81-mediated signal transduction can be administered to an individual by an appropriate route, either alone or in combination with another drug.

A variety of routes of administration are possible including, but not limited to, oral, dietary, topical, parenteral (e.g., intravenous, intraarterial, intramuscular, subcutaneous injection), and inhalation (e.g., intrabronchial, intranasal or oral inhalation, intranasal drops) routes of administration, depending on the agent and disease or condition to be treated. For respiratory allergic diseases such as asthma, inhalation is a preferred mode of administration.

Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, *Remington's Pharmaceutical Sciences*, 17th Edition, Mack Publishing Co., PA, 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The invention also pertains to assays for identifying agents which enhance or inhibit calcium independent CD81-mediated signal transduction. The assay comprises combining a cell bearing CD81 with an agent to be tested, under conditions suitable for signal transduction by CD81. The level or extent of CD81-mediated signal transduction can be measured using standard methods and compared with the level or extent of CD81-mediated signal transduction in the absence of the agent (control). An increase in the level or extent of CD81-mediated signal transduction relative to the control indicates that the agent is a promoter of CD81-mediated signal transduction; a decrease in the level or extent of CD81-mediated signal transduction relative to the control indicates that the agent is an inhibitor of CD81-mediated signal transduction.

Inhibitors or promoters of CD81-mediated signal transduction, e.g., those identified by methods described herein, can be assessed to determine their effect on cell surface receptor signaling. Inhibitors or promoters of CD81-mediated regulation of cell surface receptor signaling can be, for example, small molecules, antibodies and/or peptides. A cell bearing CD81 and an appropriate cell surface receptor (e.g., FcεRI or FcγRIII) are combined with an inhibitor or promoter of CD81-mediated signal transduction under conditions suitable for signal transduction by both CD81 and the cell surface receptor. The level or extent of cell surface receptor signaling can be measured using standard methods and compared with the level or extent of cell surface receptor signaling in the absence of the inhibitor or promoter (control). An increase in the level or extent of cell surface receptor signaling relative to the control indicates that the agent is a promoter of cell surface receptor signaling; a decrease in the level or extent of cell surface receptor signaling relative to the control indicates that the agent is an inhibitor of cell surface receptor signaling.

Cell surface receptor signaling can be measured directly, such as by measuring the level or amount of an associated signaling molecule, or indirectly, such as by a functional assay measuring level or amount of degranulation or passive cutaneous anaphylaxis.

The following Examples are offered for the purpose of illustrating the present invention and are not to be construed to limit the scope of this invention. The teachings of all references cited herein are hereby incorporated herein by reference.

EXAMPLES

Cell Culture, Reagents and Antibodies

The rat basophilic leukemia cell line (RBL-2H3) was cultured in EMEM supplemented with 16% heat-inactivated FCS, 2 mM L-glutamine and penicillin (100 U/ml)/streptomycin (50 mg/ml) (Biofluids, Rockville, Md.). NS-1 and SP2/0 myeloma cells were cultured in RPMI 1640 supplemented with 20% FCS, glutamine and antibiotics. C1.MC/C57.1 cells were cultured as described in Young et al. (*Proc. Natl. Acad. Sci. USA*, 84:9175–9179 (1987)). DNP-human serum albumin (DNP-HSA) (30–40 moles DNP/mole albumin) was purchased from Sigma Chemical Co. (St. Louis, Mo.). DNP-specific IgE supernatants were used to saturate FcεRI as described in Young et al. (*Proc. Natl. Acad. Sci. USA*, 84:9175–9179 (1987)). For PCA experiments, MOPC31c ($IgG_1$) and anti-DNP-mouse IgE (clone SPE-7) were purchased from Sigma Chemical Co. (St. Louis, Mo.) and anti-rat β2 integrin (anti-LFA-1β, CD18; clone WT.3) was purchased from Pharmigen (San Diego, Calif.). MOPC 31c and anti-DNP IgE were dialyzed to remove sodium azide before in vivo injections. Anti-rat CD81 (5D1, $IgG_1$) was purified from ascites on Protein G Sepharose (Pharmacia, Uppsala, Sweden).

Immunizations, Fusions, and FACS

Female BALB/c mice (4–8 weeks old) were immunized intraperitoneally with $25 \times 10^6$ RBL-2H3 emulsified in complete Freund's adjuvant or $50 \times 10^6$ in PBS. Mice were boosted after 2 weeks with $40 \times 10^6$ RBL-2H3 cells emulsified in incomplete Freund's adjuvant intraperitoneally or in PBS. For the final immunizations, animals were injected with $20-40 \times 10^6$ RBL-2H3 cells intraperitoneally at day-4 (fusion=day 0) and intravenous at day-3. Spleen cell preparations were fused with either NS-1 or SP2/0 myeloma cells in polyethylene glycol and plated onto normal BALB/c spleen feeder cells. To enhance the development of the hybridomas, *S. typhimurium* mitogen (Ribi ImmunoChem Research, Inc., Namilton, Mont.) was included in the culture medium from days 0–10. Hybridoma supernatants were tested after day 14 by flow cytometry for binding to RBL-2H3 using FITC-conjugated goat anti-mouse F(ab')2-specific antibody (Jackson ImmunoResearch Laboratories, Inc., West Grove, Pa.) and analyzed by flow cytometry on a FACSCAN™ flow cytometer (Becton-Dickinson, San Jose, Calif.).

From 3 separate fusions, a total of 2160 wells were plated and 622 supernatants from wells with hybridoma growth were screened by FACS for reactivity with RBL-2H3 cells. In all, 283/622 (45%) elicited detectable reactivity by FACS with membrane antigens of RBL-2H3. The screening of RBL-2H3-reactive mAbs by serotonin release assay lead to the identification of 1A12 ($IgG_{2b}$ and 5D1 ($IgG_1$), which were characterized further. Rat CD81 transfectants of were stained with purified 1A12 and 5DI (1 μg/$10^6$ cells), counterstained with goat anti-mouse F(ab')$_2$-specific antibody and analyzed by flow cytometry on a FACScan® flow cytometer.

Serotonin Release Assay and Leukotriene C4 Assays

RBL-2H3 cells were loaded with $[^{3}H]$5-hydroxytryptamine ($[^{3}H]$serotonin; 0.1–0.3 mCi/$10^5$ cells) and saturated with DNP-specific IgE in 96-well microtiter tissue culture plates ($10^5$ cells/well, 37° C., 5% $CO_2$) as described in Daron et al. (*J. Immunol.*, 149:1365–1373 (1992)). Monolayers were washed three times with buffer (glucose-saline, PIPES buffer (pH 7.2) containing (in mM) 25 PIPES, 110 NaCl, 5 KCl, 5.6 glucose, 0.4 $MgCl_2$, 1 CaCl2 and 0.1% BSA), and 25 ml of a dilution of purified antibody was added to the labeled monolayers, and plates were incubated for 30 minutes (or as indicated) at room temperature. Triggering of FcεRI was performed by the addition of DNP-HSA (final concentration 10–250 ng/ml) and plates were incubated at 37° C. (except as indicated in FIG. 7D) with control samples present on each plate. Degranulation was stopped by placing the plates on ice and by the addition of 150 μl of cold culture medium per well. 100 μl aliquots were taken from replicate wells for scintillation counting. Total cellular incorporation was determined from 1% SDS/1% NP-40 lysates.

Leukotriene C4 was measured from $10^6$ anti-DNP IgE saturated RBL-2H3 treated with 1 μg 5DI or buffer prior to triggering with 30 ng/ml DNP-HSA. Supernatants were stored at −80° C. until measurement of $LTC_4$ by specific enzyme immunoassay (Cayman Chemical, Ann Arbor, Mich.).

Immunoaffinity Chromatography, Electrophoresis, and Western Blotting

RBL-2H3 cells were cultured in routine culture medium in spinner flasks to a cell density of approximately $10^6$/ml, harvested by centrifugation and washed twice with cold PBS. Washed cells were extracted in 0.5 M $K_2HPO_4$ (pH 7.5) with proteinase inhibitors (10 µg/ml pepstatin, 5, µg/ml leupeptin, and 10 µg/ml aprotinin) at $50 \times 10^6$/ml for 60 minutes at 4° C. with frequent mixing. N-octyglucoside (10 mM) was added during the extraction to ensure protein solubility. Post-nuclear lysates were prepared by centrifugation at 15,000×g for 20 minutes at 4° C. Lysates were then passed through 0.2 mM filters to remove residual debris and passed several times over protein G-Sepharose coupled to 1A12 (2 mg/ml bed volume), washed with PBS (10 mM n-octylglucoside) and eluted with 0.2 M glycine. Tris-neutralized, concentrated extracts were reduced with β-mercaptoethanol, resolved on 12.5% preparative SDS-PAGE and transferred to Immobilon$^{SQ}$ (Millipore, Bedford, Mass.). The membrane was stained with amido black and the Mr 25 kDa band was excised, eluted, alkylated and digested overnight with Lys-C. Peptides were separated by reverse phase-HPLC and the peptide peak eluting at 36 minutes was sequenced. Subsequent cloning and expression of rat CD81 cDNA from RBL-2H3 confirmed that 1A12 and 5D1 recognize rat CD81 and that CD81 cross-linking inhibits FcεRI-mediated mast cell degranulation.

For anti-phosphotryosine Western blots, 0.5% TritonX-100 (BBS, proteinase inhibitors) extracts were immunoprecipitated overnight with 2 µg of anti-phosphotryosine mAb 4G10 bound to protein A-Sepharose beads (4° C. with rotation). Beads were washed with lysis buffer, eluted, resolved on 12.5% SDS-PAGE, transferred to nitrocellulose membranes and immunoblotted with 1 µg/ml 4G10 mAb, followed by incubation with HRP-conjugated anti-mouse IgG secondary antibodies and development with chemiluminescence substrates (Renaissance, Dupont/NEN, Boston, Mass.).

Construction and Screening of RBL-2H3 cDNA Library in UNI-ZAP™

Poly A+ mRNA was isolated from RBL-2H3, reverse-transcribed into cDNA, size-fractionated on Sephacryl S-500 spin columns and ligated into UNI-ZAP-XR lambda vector according to the manufacturer's instructions (Stratagene, La Jolla, Calif.). After rescue of the cDNA inserts and appropriate restriction enzyme digests, it was determined that 96% of the plasmids contained inserts, with an average size of 1.7 kB. $5 \times 10^5$ plaques were screened with $^{32}$P-labeled mouse CD81 cDNA probe. After hybridization, nitrocellulose filters were washed once with 2×SSC containing 0.1% SDS (room temperature) and 3 times with 0.5×SSC containing 0.1% SDS at 50° C. Filters were autoradiographed and plaques picked and eluted. Candidate plaques were subjected to three additional rounds of plaque purification before rescue of the cDNA inserts into pBluescript. Sequencing was performed on eleven isolates and all were found to align with accession number U19894 isolated from rat brain (Geisert, Jr., et al., Neurosci. Lett. 133: 262–266 (1991); Irwin and Geisert, Jr., Neurosci. Lett., 154:57–60 (1993); Geisert, Jr., et al., J. Neurosci., 16:5478–5487 (1996)).

Transfections: Rat CD81 cDNA from two isolates was sub-cloned into the pBJlneo expression vector (Lin et al., Cell, 85:985–995 (1996)) and 20 µg of ethanol-precipitated DNA was used for electroporation of C1.MC/C57.1 cells (1050 µF, 270 v). Selection of stable transfectants was initiated 48 hours later by replating at 500–10,000 cells per well with 2 mg/ml G418 (Life Technologies, Grand Island, N.Y.).

Confocal Microscopy: After overnight adherence and saturation of FcεRI with DNP-specific IgE, RBL-2H3 cells were washed with buffer and incubated with 3 µM fluo3/AM (Molecular Probes, Eugene, Oreg.) and 0.2 mg/ml Pluronic (Molecular Probes) at 37° C. for 30 minutes (5% $CO_2$) in a buffer containing 140 mM NaCl, 5 mM KCl, 1 mM $MgCl_2$, 1 mM $CaCl_2$, 10 mM glucose, and 1 mM Na-HEPES (pH 7.4). Dye-loaded cells were then washed once with the same buffer before preincubation (30 minutes, room temperature) with buffer (±5D1, 1 µg/chamber/$10^5$ cells) and triggering with 100 ng/ml DNP-HSA. $Ca^{2+}$ measurements in single cells were monitored using a laser-scanning confocal microscope (LSM4, Zeiss, New York, N.Y.) equipped with an argon/kryton laser to excite the dye at 488 nm. Fluorescence emission above 510 nm was measured after placing a long pass filter in front of the photomultiplier tube. The confocal system was employed in slow scan mode and fluorescence images were collected every 5 seconds. Fluo-3 fluorescence measurements were normalized by dividing the average fluorescence intensity (F) occurring during the course of the experiment to the average fluorescence intensity determined at the beginning of the experiment ($F_0$). All measurements were performed at 22–24° C.

Passive Cutaneous Anaphylaxis in Rats

Figure 11A:
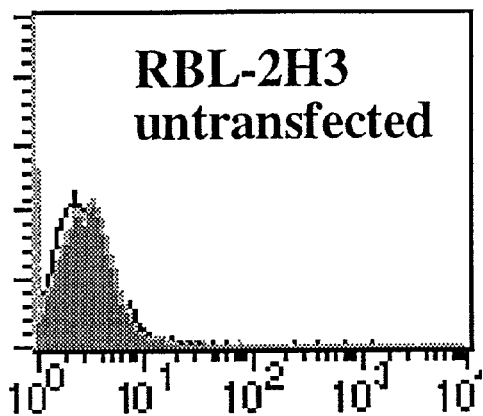
FIGS. 11A–11D are the results of FACS analysis of 3 stable mouse FcγRIII RBL-2H3 transfectants after staining with 2.4G2 and FITC-anti-rat IgG.
Figure 11B:
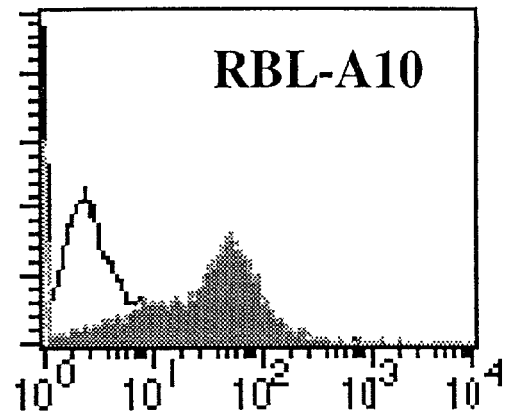
Figure 11C:
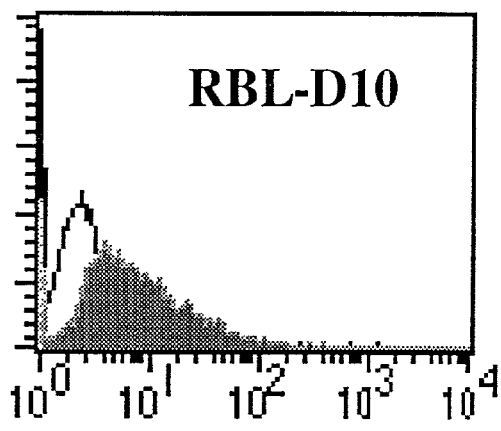
Figure 11D:
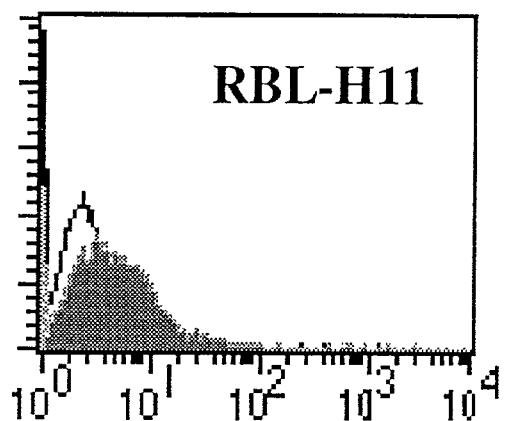
Figure 12A:
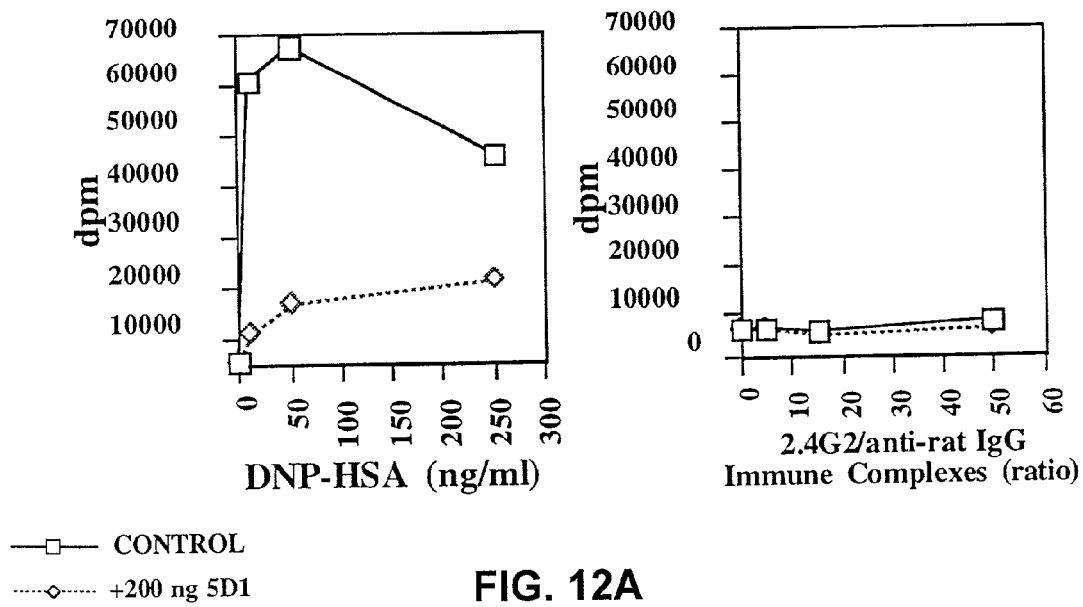
FIGS. 12A–12D is a set graphs illustrating that DNP-HSA induces IgE-mediated degranulation in four different cell lines (untransfected RBL-2H3, FIG. 12A; RBL-A10, FIG 12B; RBL-D10, FIG. 12C; and RBL-H11, FIG. 12D), and that this degranulation is inhibitable by anti-CD81 mAb 5D1.
Figure 12B:
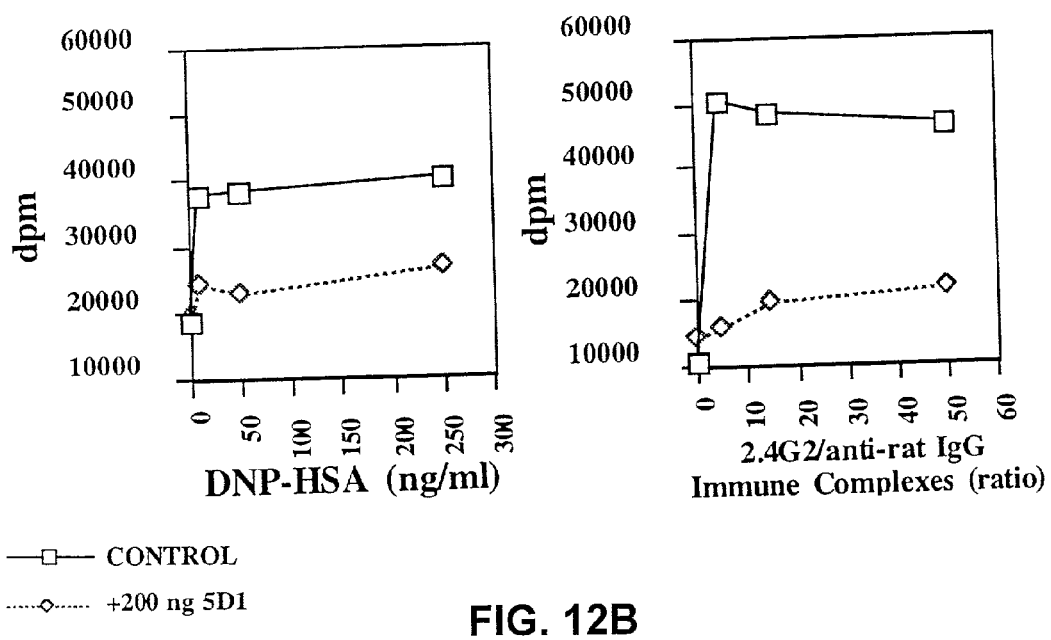
Figure 12C:
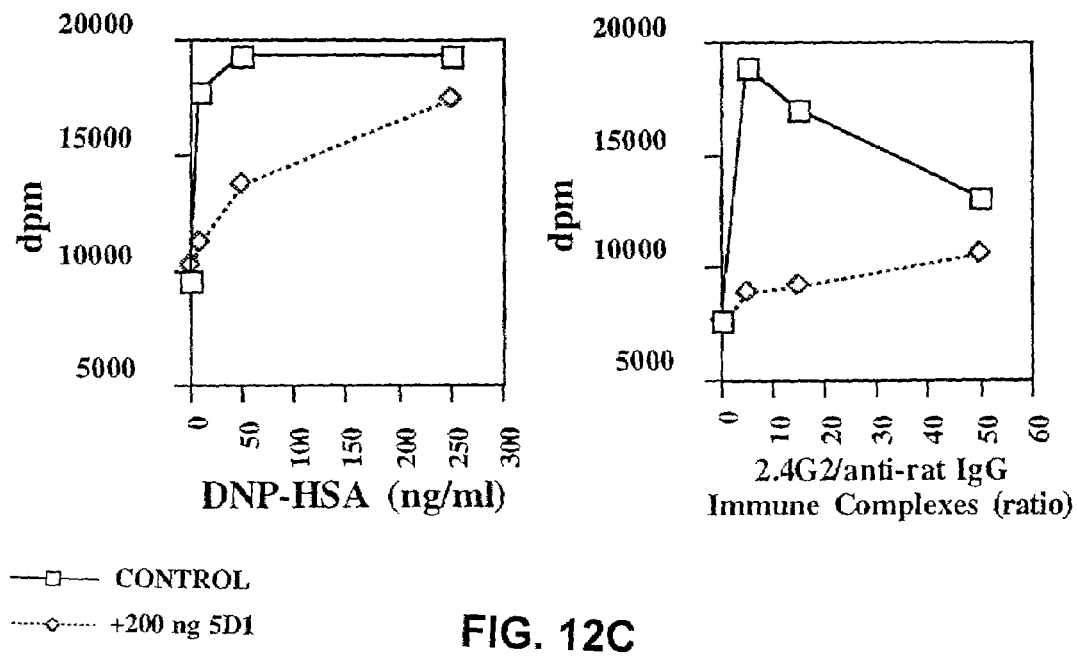
Figure 12D:
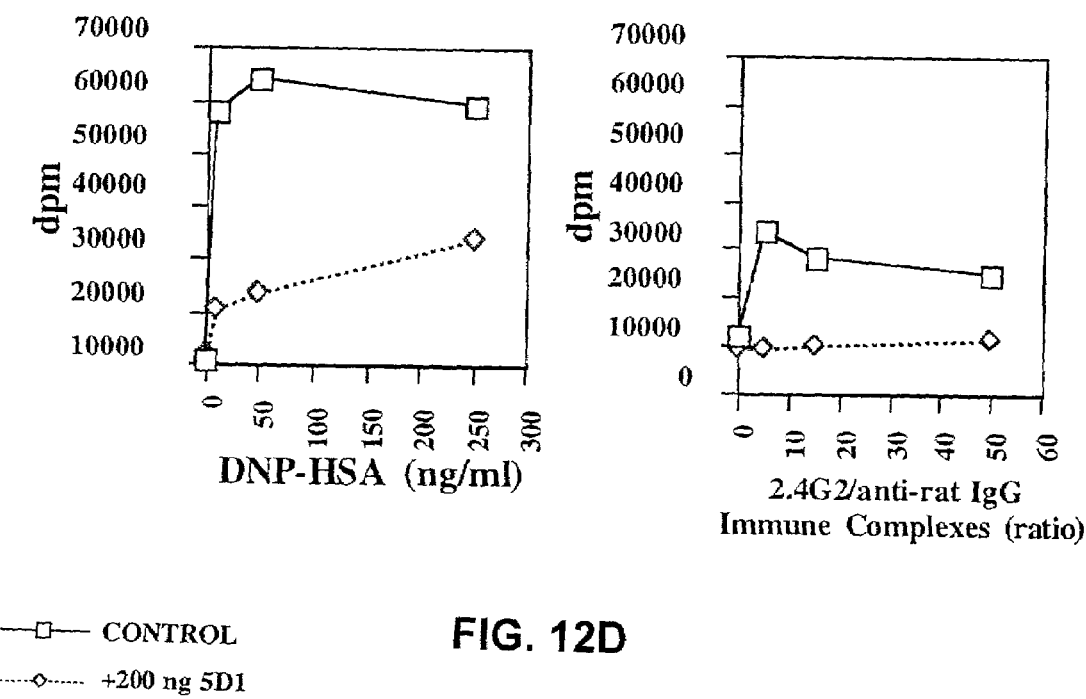

Male Wistar rats (275–300 g) were used in these experiments. Rats were first anesthetized with ether, then back skin hair was shaved and rats were injected intradermally with 50 µl containing 100 ng anti-DNP IgE or 25 ng anti-DNP-IgE mixed with 50 µg of MOPC 31c (mouse $IgG_1$, specificity unknown) or 5D1 (mouse $IgG_1$, anti-rat CD81). Control sites received buffer alone (PBS containing 10 µg/ml mouse serum albumin; Sigma Chemical Co., St. Louis, Mo.). Sites were marked on the skin for orientation and rats that received 100 ng anti-DNP injections received a second injection 21 hours later with 50 µg of 5D1 or anti-rat LFA-1β (CD18; mouse $IgG_1$) into previously injected sites. Sites receiving IgE and $IgG_1$ were injected in triplicate on the same rat. Twenty-four hours after IgE injections, animals received 1 ml of 1 mg/ml DNP-HSA containing 1% Evan's Blue dye injected intravenously under ether anesthesia. Thirty minutes after intravenous injection, rats were sacrificed, and punch biopsies (2.5 cm$^2$) were obtained, minced and extracted 3 times with hot formamide (80° C., 3 hours) (Dombrowicz et al., J. Clin. Invest., 99:915–925 (1997)). Pooled samples from tissue sites were centrifuged and absorbence at 610 nm ($A_{610}$) was measured. $A_{610}$ values were converted to µg Evanis blue based on a standard curve of dilutions of Evan's Blue in formamide. Inhibition of Signaling Elicited Through the Low Affinity IgG Receptor FcRγIII RBL-2H3 cells express FcεRI, CD81 and endogenous rat FcγRIII receptors. However, no high-affinity reagent (antibody) is available to trigger these receptors on RBL-2H3; the 2.4G2 antibody (anti-mouse FcγRII/FcγRIII) was used for this purpose. To demonstrate that CD81 stimulation inhibits degranulation induced through FcγRIII signaling as it does for FcεRI, murine FcγRIIIα chain cDNA was expressed in RBL-2H3 cells. FcRγ cDNA was co-transfected to assist in the surface expression of FcγRIII complexes. In FIGS. 11A–11D, the histograms of 3 stable mouse FcγRIII RBL-2H3 transfectants are shown after staining with 2.4G2 and FITC-anti-rat IgG. Untransfected RBL-2H3 cells exhibit no detectable binding of 2.4G2 (FIG. 11A).

FcγRIII binding of IgG is detectable only when IgG is present in the form of IgG-containing immune complexes which cross-link FcγRIII receptors and initiate intracellular signals. One of the methods of triggering FcγRIII is through stimulation with crosslinked anti-FcγRIII antibodies. In FIG. 12, RBL-2H3 and FcγRIII-transfectants of RBL-2H3 were loaded with $^3$H-serotonin in the presence (DNP-HSA stimulation) or absence (immune complex stimulation) of DNP-specific IgE. After overnight incubation, cells were washed and incubated with culture media or media containing 200 ng of anti-rat CD81 mAb 5D1 prior to triggering with optimized concentrations of DNP-HSA or with preformed immune complexes of 2.4G2/anti-rat IgG F(ab')$_2$. Degranulation was allowed to proceed for 30 minutes at 37° C. and released $^3$H-serotonin was quantitated by scintillation counting. As shown in FIG. 12, DNP-HSA induces IgE-mediated degranulation in all four cell lines which is inhibitable by anti-CD81 mAb 5D1. 2.4G2/anti-rat IgG F(ab')2 preformed complexes, but not anti-rat IgG F(ab)2 alone, induce degranulation only in cells expressing mFcγRIII receptors (RBL-2H3 transfectants A10, D10 and H11), a process which is also inhibitable by preincubation with 5D1. This data provides the identification of CD81 as a common inhibitor of both FcεRI and FcγRIII.

Results

Figure 4:
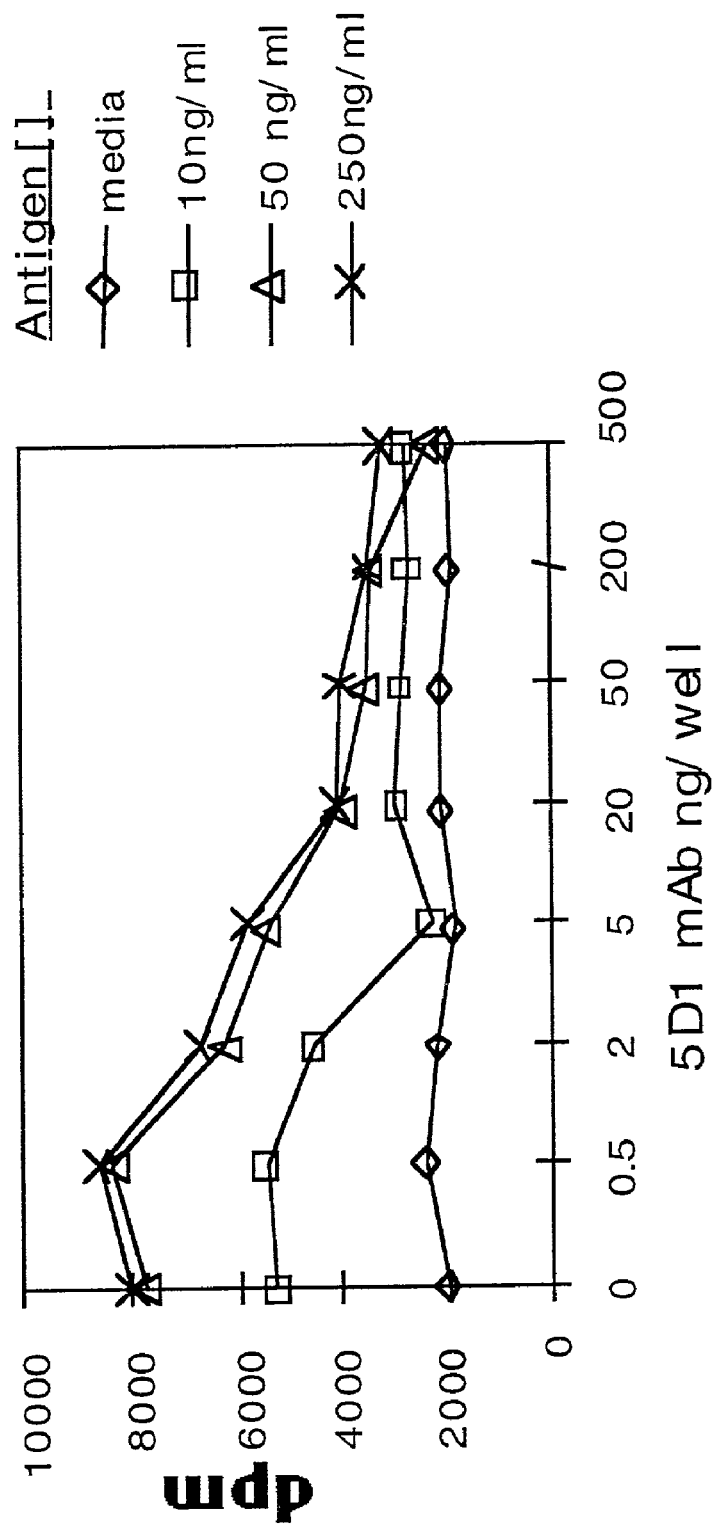
FIG. 4 illustrates 5D1 mAb inhibition of FcεRI-mediated degranulation in RBL-2H3 cells.
Figure 6A:
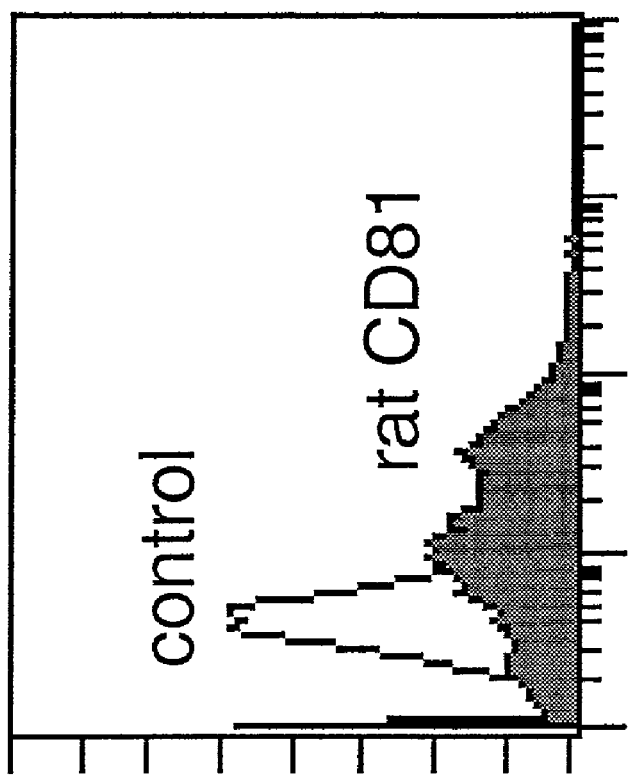
FIGS. 6A–6B are the results of FACS analysis illustrating expression of rat CD81 in CHO and NIH-3T3 cells.
Figure 6B:
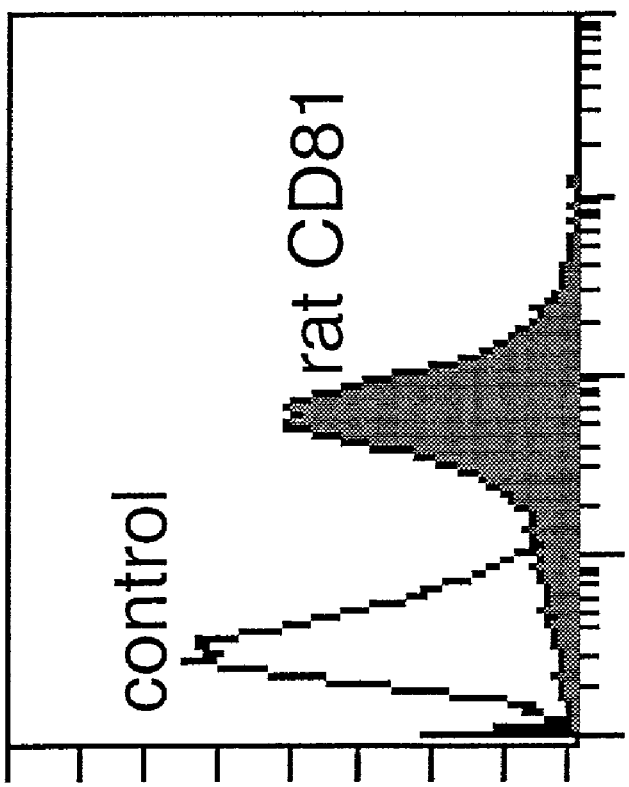

5D1 mAb inhibits FcεRI-mediated degranulation by antigen. From 3 separate fusions, a total of 2160 wells were plated and 622 supernatants from wells with hybridoma growth were screened by FACS for reactivity with the immunizing RBL-2H3 cells (see Table 1). In all, 283/622 elicited detectable reactivity by FACS with membrane antigens of RBL-2H3. Supernatants from the positive hybridomas were then tested for inhibition of FcεRI-mediated degranulation. RBL-2H3 cells exhibit a reproducible degranulation profile to FcεRI-IgE stimulation by the corresponding antigen DNP-HSA. Detectable serotonin release is observed with 1 ng/ml concentrations of DNP-HSA; maximal serotonin release occurs with approximately 50 ng/ml, and at concentrations greater than 1 mg/ml DNP-HSA degranulation is inhibited, presumably because of the diminished ability of large FcεRI-IgE aggregates to signal. In FIG. 4, purified 5D1 mAb inhibits IgE-mediated degranulation in RBL-2H3 cells stimulated with 10, 50 or 250 ng/ml DNP-HSA, with maximal inhibition occurring at 5–20 ng/$10^5$ RBL-2H3 cells. RBL-2H3 cells were saturated with DNP-specific IgE and labeled with 3H-hydroxytryptamine (serotonin) 0.2 mCi/$10^5$ cells/well (0.32 cm$^2$), washed three times with triggering buffer and incubated for 30 minutes at room temperature with the indicated concentration of affinity-purified 5D1 mAb in 25 ml total volume. After incubation, cells were challenged with 25 μl of 2× dilution of pre-warmed DNP-HSA and triggered for 30 minutes (37° C., 5% $CO_2$). Release was terminated by the addition of 150 μl of ice-cold triggering buffer and by placing the plates on ice. 100 μl aliquots of released radioactivity as well as SDS cell lysates were then harvested and scintillation counted. Degranulation-inhibitory mAb binding has little or no effect on IgE or anti-FcεRIα binding.

TABLE 1

Binding inhibition of FITC-conjugated mAbs directed to RBL-2H3 surface antigens

| Preincubation | Specificity | Median Fluorescence Intensity (mCi) | | | | FITC-conjugated mAbs |
|---|---|---|---|---|---|---|
| | | 1A12 | IgE | 4H7 | 3A9 | |
| — | | — | 37.9 | 75.0 | 83.5 | 289.0 |
| 1A12 | | | ND | 61.0 | 83.5 | 289.0 |
| 5D1 | | | 6.5 | ND | ND | ND |
| 4H7 | rat FcεRIα | 38.2 | 6.4 | 7.2 | 38.5 | |
| 3A9 | rat FcεRIα | 37.5 | 6.5 | 6.8 | 13.4 | |
| BC4 | rat FcεRIα | 38.5 | 5.8 | 5.4 | 5.9 | |
| 5.14 | rat FcεRIα | 39.6 | 5.5 | 84.3 | 161.0 | |
| AA4 | ganglioside $G_{d1b}$ | ND | 12.3 | 59.3 | 201.7 | |

$10^6$ RBL-2H3 cells were incubated on ice with a saturating amount of unconjugated antibody (preincubation) for 30 minutes prior to the addition (without washes) of a titered (subsaturating) concentration of FITC-conjugated mAb. After washes, stained cells were analyzed by FACS and mean values histgram peaks converted to median fluorescent intensity (MCI) units.

Equivalents

While this invention has been particularly shown and described with references to preferred embodiments thereof, it will be understood by those skilled in the art that various changes in form and details may be made therein without departing from the spirit and scope of the invention as defined by the following claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of treating an allergic or inflammatory condition associated with FcεRI-mediated degranulation and/or FcγRIII-mediated degranulation comprising administering to a mammal an effective amount of an antibody that binds to CD81 and inhibits FcεRI-mediated degranulation and/or FcγRIII-mediated degranulation.

2. The method of claim 1, wherein the allergic or inflammatory condition is selected from the group consisting of asthma, hay fever and atopic eczema.

3. The method of claim 1, wherein the antibody that binds to CD81 is a monoclonal antibody.

4. The method of claim 1 wherein the allergic or inflammatory condition is passive cutaneous anaphylaxis.

5. The method of claim 1, wherein the antibody does not alter one or more of FcεRI-induced tyrosine phosphorylation, FcεRI-induced intracellular calcium mobilization and leukotriene $C_4$ ($LTC_4$) production.

6. The method of claim 1, wherein the allergic or inflammatory condition associated with FcεRI-mediated degranulation and/or FcγRIII-mediated. degranulation is an allergic or inflammatory condition associated with FcγRIII-mediated degranulation.

7. The method of claim 1, wherein the allergic or inflammatory condition associated with FcεRI-mediated degranulation and/or FcγRIII-mediated degranulation is an allergic or inflammatory condition associated with FcγRIII-mediated degranulation.

8. The method of claim 1, wherein the allergic or inflammatory condition is asthma.

9. The method of claim 1 further comprising administering a physiologically acceptable carrier.

10. The method of claim 1, wherein the antibody that binds to CD81 is a polyclonal antibody.

11. The method of claim 1, wherein the antibody that binds to CD81 is mAb 5D1.

12. The method of claim 1, wherein the antibody that binds to CD81 is mAb 1A12.

13. The method of claim 1, wherein the allergic or inflammatory condition is an allergic condition.

14. The method of claim 1, wherein the allergic or inflammatory condition is an anaphylactic reaction.

15. The method of claim 1, wherein the allergic or inflammatory condition is characterized by mast cell activation.

16. The method of claim 1, wherein the allergic or inflammatory condition is characterized by basophil activation.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: rattus
<220> FEATURE:
<221> NAME/KEY: VARIANT
<222> LOCATION: 12
<223> OTHER INFORMATION: Xaa = Any Amino Acid

<400> SEQUENCE: 1

Phe Tyr Asp Gln Ala Leu Gln Gln Ala Val Met Xaa Asp Asp
 1               5                  10

<210> SEQ ID NO 2
<211> LENGTH: 14
<212> TYPE: PRT
<213> ORGANISM: rattus

<400> SEQUENCE: 2

Phe Tyr Asp Gln Ala Leu Gln Gln Ala Val Met Asp Asp Asp
 1               5                  10

<210> SEQ ID NO 3
<211> LENGTH: 14
<212> TYPE: PRT
<213> ORGANISM: Mus musculus

<400> SEQUENCE: 3

Phe Tyr Asp Gln Ala Leu Gln Gln Ala Val Val Asp Asp Asp
 1               5                  10

<210> SEQ ID NO 4
<211> LENGTH: 14
<212> TYPE: PRT
<213> ORGANISM: Homo sapiens

<400> SEQUENCE: 4

Phe Tyr Asp Gln Ala Leu Gln Gln Ala Val Met Asp Asp Asp
 1               5                  10
```